(12) United States Patent
Williams et al.

(10) Patent No.: US 11,571,208 B2
(45) Date of Patent: Feb. 7, 2023

(54) SURGICAL BUTTRESS LOADING UNITS

(71) Applicant: Covidien LP, Mansfield, MA (US)

(72) Inventors: Justin Williams, Southbury, CT (US); Christopher Switalski, Glastonbury, CT (US); Anthony L. Ceniccola, Hamden, CT (US); Russell Pribanic, Roxbury, CT (US); Stanislaw Marczyk, Stratford, CT (US)

(73) Assignee: Covidien LP, Mansfield, MA (US)

( * ) Notice: Subject to any disclaimer, the term of this patent is extended or adjusted under 35 U.S.C. 154(b) by 657 days.

(21) Appl. No.: 16/599,468

(22) Filed: Oct. 11, 2019

(65) Prior Publication Data

US 2021/0106329 A1    Apr. 15, 2021

(51) Int. Cl.
*A61B 17/072* (2006.01)
*A61B 17/11* (2006.01)

(52) U.S. Cl.
CPC ............ *A61B 17/072* (2013.01); *A61B 17/11* (2013.01); *A61B 2017/07264* (2013.01); *A61B 2017/07271* (2013.01)

(58) Field of Classification Search
CPC ........ A61B 17/072; A61B 2017/07214; A61B 2017/07257; A61B 2017/07264; A61B 17/11; A61B 17/105
See application file for complete search history.

(56) References Cited

U.S. PATENT DOCUMENTS

| 3,054,406 A | 9/1962 | Usher |
|---|---|---|
| 3,124,136 A | 3/1964 | Usher |
| 3,364,200 A | 1/1968 | Ashton et al. |
| 3,499,591 A | 3/1970 | Green |
| 3,797,494 A | 3/1974 | Zaffaroni |

(Continued)

FOREIGN PATENT DOCUMENTS

| CA | 2282761 A1 | 9/1998 |
|---|---|---|
| DE | 1602563 U | 3/1950 |

(Continued)

OTHER PUBLICATIONS

Australian Examination Report No. 1 corresponding to AU 2014200793 dated Sep. 2, 2017.

(Continued)

*Primary Examiner* — Anna K Kinsaul
*Assistant Examiner* — Himchan Song
(74) *Attorney, Agent, or Firm* — Carter, DeLuca & Farrell LLP

(57) ABSTRACT

A surgical buttress loading assembly includes a surgical buttress applicator, an anvil buttress, and a cartridge buttress. The surgical buttress applicator includes an anvil buttress loading unit defining a buttress cavity and a strap cavity therein, and a cartridge buttress loading unit defining a buttress cavity and a strap cavity therein. The anvil buttress includes a tubular body disposed within the buttress cavity of the anvil buttress loading unit and a strap extending from the tubular body and positioned within the strap cavity of the anvil buttress loading unit. The cartridge buttress includes a tubular body disposed within the buttress cavity of the cartridge buttress loading unit and a strap extending from the tubular body and positioned within the strap cavity of the cartridge buttress loading unit.

13 Claims, 23 Drawing Sheets

(56) References Cited

U.S. PATENT DOCUMENTS

| | | |
|---|---|---|
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |

(56) References Cited

U.S. PATENT DOCUMENTS

| | | | |
|---|---|---|---|
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,819,896 B2 | 10/2010 | Racenet |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,256,656 B2 | 9/2012 | Milliman et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, Iv et al. |
| 8,540,131 B2 | 9/2013 | Swayze |

(56) References Cited

U.S. PATENT DOCUMENTS

| | | |
|---|---|---|
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek et al. |
| 9,655,620 B2 | 5/2017 | Prescott et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 9,918,713 B2 | 3/2018 | Zergiebel et al. |
| 9,931,116 B2 | 4/2018 | Racenet et al. |
| 10,022,125 B2 | 7/2018 | Stopek et al. |
| 10,098,639 B2 | 10/2018 | Hodgkinson |
| 10,111,659 B2 | 10/2018 | Racenet et al. |
| 10,154,840 B2 | 12/2018 | Viola et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0006429 A1 | 1/2005 | Wales et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Dray et al. |
| 2006/0190027 A1 | 8/2006 | Downey |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |

(56) References Cited

U.S. PATENT DOCUMENTS

| | | |
|---|---|---|
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2013/0153636 A1 | 6/2013 | Shelton, IV et al. |
| 2013/0153641 A1 | 6/2013 | Shelton, IV et al. |
| 2013/0214030 A1* | 8/2013 | Aronhalt ............ A61B 17/0644 227/176.1 |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0224686 A1 | 8/2014 | Aronhalt et al. |
| 2014/0239047 A1 | 8/2014 | Hodgkinson et al. |
| 2015/0041347 A1 | 2/2015 | Hodgkinson |
| 2015/0133995 A1 | 5/2015 | Shelton, IV et al. |
| 2015/0157320 A1 | 6/2015 | Zergiebel et al. |
| 2015/0157321 A1 | 6/2015 | Zergiebel et al. |
| 2015/0209045 A1 | 7/2015 | Hodgkinson et al. |
| 2015/0231409 A1 | 8/2015 | Racenet et al. |
| 2015/0327864 A1 | 11/2015 | Hodgkinson et al. |
| 2015/0351758 A1* | 12/2015 | Shelton, IV ....... A61B 17/0644 606/219 |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0128694 A1 | 5/2016 | Baxter, III et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0220257 A1 | 8/2016 | Casasanta et al. |
| 2016/0249923 A1 | 9/2016 | Hodgkinson et al. |
| 2016/0270793 A1 | 9/2016 | Carter et al. |
| 2016/0278774 A1* | 9/2016 | Shelton, IV ......... A61B 17/068 |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0119390 A1 | 5/2017 | Schellin et al. |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |
| 2018/0125491 A1 | 5/2018 | Aranyi |
| 2018/0140301 A1 | 5/2018 | Milliman |
| 2018/0168654 A1 | 6/2018 | Hodgkinson et al. |
| 2018/0214147 A1 | 8/2018 | Merchant et al. |
| 2018/0229054 A1 | 8/2018 | Racenet et al. |
| 2018/0235611 A1* | 8/2018 | Harris ............... A61B 17/07207 |
| 2018/0235626 A1* | 8/2018 | Shelton, IV ..... A61B 17/07207 |
| 2018/0250000 A1 | 9/2018 | Hodgkinson et al. |
| 2018/0256164 A1 | 9/2018 | Aranyi |
| 2018/0296214 A1 | 10/2018 | Hodgkinson et al. |
| 2018/0310937 A1 | 11/2018 | Stopek et al. |
| 2018/0360460 A1 | 12/2018 | Mozdzierz et al. |
| 2019/0021734 A1 | 1/2019 | Hodgkinson |
| 2019/0059878 A1 | 2/2019 | Racenet et al. |
| 2019/0083087 A1 | 3/2019 | Viola et al. |
| 2019/0343520 A1 | 11/2019 | Williams et al. |
| 2019/0343521 A1 | 11/2019 | Williams et al. |

FOREIGN PATENT DOCUMENTS

| | | |
|---|---|---|
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 9005489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010075298 A2 | 7/2010 |

OTHER PUBLICATIONS

Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Chinese First Office Action corresponding to Patent Application CN 201410588811.8 dated Dec. 5, 2017.
European Office Action corresponding to Patent Application EP 16 16 6367.9 dated Dec. 11, 2017.
Chinese First Office Action corresponding to Patent Application CN 201610279682.3 dated Jan. 10, 2018.
Japanese Office Action corresponding to Patent Application JP 2013-154561 dated Jan. 15, 2018.
Australian Examination Report No. 1 corresponding to Patent Application AU 2017225037 dated Jan. 23, 2018.
Japanese Office Action corresponding to Patent Application JP 2013-229471 dated May 1, 2018.
Canadian Office Action corresponding to Patent Application CA 2,790,743 dated May 14, 2018.
European Office Action corresponding to Patent Application EP 14 15 7195.0 dated Jun. 12, 2018.
Extended European Search Report corresponding to Patent Application EP 12196912.5 dated Feb. 1, 2016.
Chinese Second Office Action corresponding to Patent Application CN 201610279682.3 dated Aug. 8, 2018.

(56) References Cited

OTHER PUBLICATIONS

Chinese Second Office Action corresponding to Patent Application CN 201410588811.8 dated Aug. 27, 2018.
Extended European Search Report corresponding to Patent Application EP 18160809.2 dated Sep. 18, 2018.
Extended European Search Report corresponding to Patent Application EP 18192317.8 dated Dec. 20, 2018.
Extended European Search Report corresponding to Patent Application EP 18190154.7 dated Feb. 4, 2019.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).
Extended European Search Report corresponding to EP 13 15 4571.7, completed Oct. 10, 2014 and dated Oct. 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
European Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to ON 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2 016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).

(56) References Cited

OTHER PUBLICATIONS

European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
Extended European Search Report dated Mar. 4, 2021 corresponding to counterpart Patent Application EP 20201039.3.
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016.
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2 017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.

(56) References Cited

OTHER PUBLICATIONS

Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.
Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.

* cited by examiner

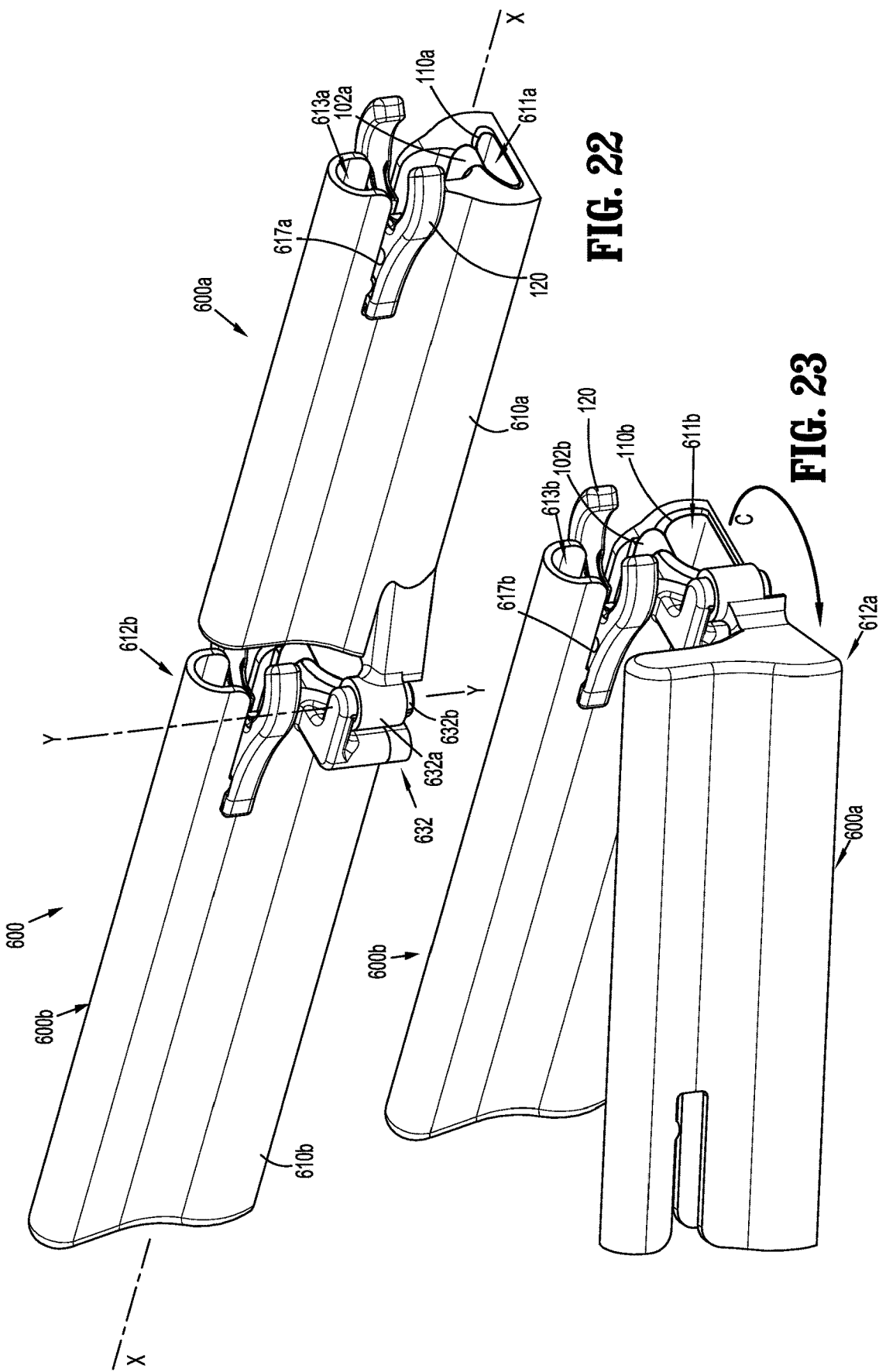

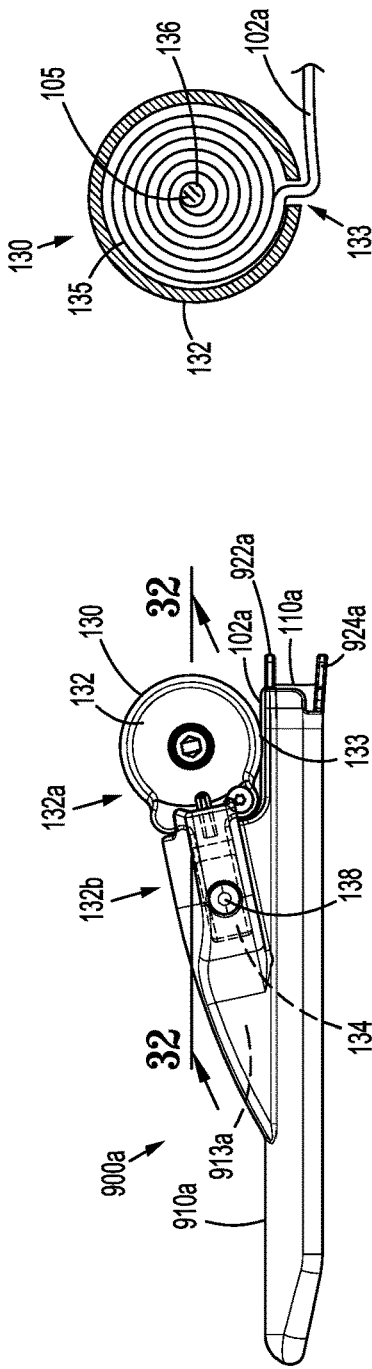
FIG. 31
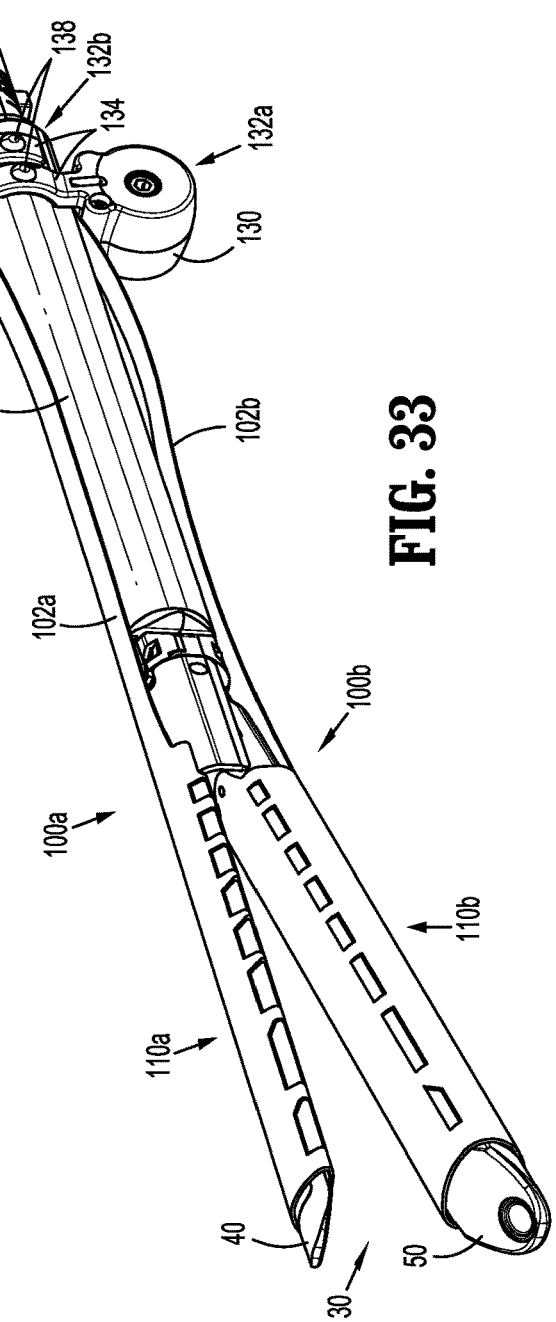
FIG. 32
FIG. 33

SURGICAL BUTTRESS LOADING UNITS

TECHNICAL FIELD

The present application relates to surgical buttress loading units for use with surgical stapling apparatus and more particularly, to surgical buttress loading units for releasably securing surgical buttresses to surgical stapling apparatus.

BACKGROUND

Surgical stapling apparatus are employed by surgeons to sequentially or simultaneously apply one or more rows of fasteners, e.g., staples or two-part fasteners, to body tissue for the purpose of joining segments of body tissue together and/or creating anastomoses. Linear surgical stapling apparatus generally include a pair of jaws or finger-like structures between which the body tissue to be joined is placed. When the linear surgical stapling apparatus is actuated, or "fired", longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in one of the jaws of the apparatus to cut the body tissue between the lines of staples.

Surgical supports, e.g., meshes or buttress materials, may be used in combination with surgical stapling apparatus to bridge, repair, and/or reinforce tissue defects within a patient such as those occurring, for example, in the abdominal wall, chest wall, diaphragm, or musculo-aponeurotic areas of the body. The buttress material reinforces the staple line as well as covers the juncture of the tissues to reduce leakage prior to healing. The buttress material can help promote proper staple formation while reducing twisting/malformation caused by any misalignment of tissue and/or unusual or non-uniform tissue. The buttress material can also provide support to weakened tissue, or help address differences in the thickness of tissues.

SUMMARY

Surgical buttress loading units of the present disclosure are utilized to load buttress materials onto surgical stapling apparatus.

In an aspect of the present disclosure, a surgical buttress loading assembly includes a surgical buttress applicator, an anvil buttress, and a cartridge buttress. The surgical buttress applicator includes an anvil buttress loading unit and a cartridge buttress loading unit. The anvil buttress loading unit defines a buttress cavity and a strap cavity therein. The cartridge buttress loading unit defines a buttress cavity and a strap cavity therein. The anvil buttress includes a tubular body disposed within the buttress cavity of the anvil buttress loading unit and a strap extending from the tubular body and positioned within the strap cavity of the anvil buttress loading unit. The cartridge buttress includes a tubular body disposed within the buttress cavity of the cartridge buttress loading unit and a strap extending from the tubular body and positioned within the strap cavity of the cartridge buttress loading unit.

In some aspects, the surgical buttress loading assembly includes a first clip secured to the strap of the anvil buttress and a second clip secured to the strap of the cartridge buttress. The first and second clips may be releasably secured to the respective anvil and cartridge buttress loading units. In certain aspects, the first and second clips are each partially disposed within the strap cavity of the respective anvil and cartridge buttress loading units.

The anvil and cartridge buttress loading units may each include first and second tabs extending proximally from the respective buttress cavities. The first and second tabs may be configured to engage the respective anvil and cartridge buttresses to retain the tubular body portions within the buttress cavity in an open configuration.

The anvil buttress loading unit may be disposed proximal of the cartridge buttress loading unit.

The anvil and cartridge buttress loading units may be separate from each other and include indicia indicating the loading sequence onto a surgical stapler.

In some aspects, a hinge interconnects the anvil and cartridge buttress loading units about a distal end portion of the surgical buttress applicator so that the anvil and cartridge buttress loading units are movable between approximated and unapproximated positions. In some aspects, a hinge interconnects the anvil and cartridge buttress loading units such that in a first position, the anvil buttress loading unit is longitudinally aligned with the cartridge buttress loading unit and blocks the buttress cavity of the cartridge buttress loading unit and, in a second position, the anvil buttress loading unit is rotated laterally so that the buttress cavity of the cartridge buttress loading unit is unblocked.

The anvil and cartridge buttress loading units may be longitudinally slidable relative to each other such that in a first position, the anvil buttress loading unit is proximal of the cartridge buttress loading unit and, in a second position, the anvil and cartridge buttress loading units are aligned.

In some aspects, the first clip blocks the buttress cavity of the cartridge buttress loading unit. In certain aspects, the first clip partially extends into the buttress cavity of the cartridge buttress loading unit. In certain aspects, the first clip extends laterally across the buttress cavity of the cartridge buttress loading unit and the second clip extends longitudinally from the buttress cavity of the cartridge buttress loading unit.

In another aspect of the present disclosure, a surgical buttress applicator includes an anvil buttress loading unit and a cartridge buttress loading unit. The anvil buttress loading unit defines a buttress cavity and a strap cavity therein, and the cartridge buttress loading unit defines a buttress cavity and a strap cavity therein.

In yet another aspect of the present disclosure, a method of loading surgical buttresses onto a surgical stapler includes: sliding an anvil assembly of a surgical stapler into a tubular body of an anvil buttress disposed within a buttress cavity defined in an anvil buttress loading unit of a surgical buttress applicator; attaching a clip to an elongate tubular body portion of the surgical stapler, the clip secured to a strap of the anvil buttress, and the strap secured to the tubular body of the anvil buttress; and removing the surgical buttress applicator from the anvil assembly of the surgical stapler, leaving the tubular body of the anvil buttress disposed over the anvil assembly and the strap of the anvil buttress extending along the elongate tubular body portion of the surgical stapler.

The method may further include detaching the clip from the surgical buttress applicator prior to attaching the clip to the elongate tubular body portion of the surgical stapler.

In some aspects, attaching the clip further includes engaging a pair of fingers of the clip with the elongate tubular body portion adjacent to a handle assembly of the surgical stapler.

The strap of the anvil buttress may be disposed within a strap cavity defined in the anvil buttress loading unit of the surgical buttress applicator and attaching the clip to the elongate tubular body portion may include unfurling the strap from the strap cavity.

In some aspects, the method further includes: sliding a staple cartridge assembly of the surgical stapler into a tubular body of a cartridge buttress disposed within a buttress cavity defined in a cartridge buttress loading unit of the surgical buttress applicator; attaching a clip to the elongate tubular body portion of the surgical stapler, the clip secured to a strap of the cartridge buttress, and the strap secured to the tubular body of the cartridge buttress; and removing the surgical buttress applicator from the staple cartridge assembly of the surgical stapler, leaving the tubular body of the cartridge buttress disposed over the staple cartridge assembly and the strap of the cartridge buttress extending along the elongate tubular body portion of the surgical stapler.

The method may further include: firing the surgical stapler to drive staples through a buttress portion of the tubular body of the anvil buttress; and pulling the strap of the anvil buttress to separate the strap and a folded portion of the tubular body of the anvil buttress from the buttress portion.

In another aspect of the present disclosure, a surgical buttress loading assembly includes an anvil buttress loading unit, a cartridge buttress loading unit, a first clip, a second clip, an anvil buttress, and a cartridge buttress. The anvil and cartridge buttress loading units each define a buttress cavity and a clip cavity therein. The first clip is at least partially disposed within the clip cavity of the anvil buttress loading unit, and defines a strap cavity therein. The second clip is at least partially disposed within the clip cavity of the cartridge buttress loading unit, and defines a strap cavity therein. The anvil buttress includes a tubular body disposed within the buttress cavity of the anvil buttress loading unit and a strap extending from the tubular body and position within the strap cavity of the first clip. The cartridge buttress includes a tubular body disposed within the buttress cavity of the cartridge buttress loading unit and a strap extending from the tubular body and positioned within the strap cavity of the second clip.

The anvil and cartridge buttress loading units may each include first and second tabs extending proximally from the respective buttress cavities. The first and second tabs may be configured to engage the respective anvil and cartridge buttresses to retain the tubular body portions within the buttress cavities in an open configuration.

In some aspects, each of the first and second clips includes a boss releasably engageable with a body of the respective anvil and cartridge buttress loading units.

The first and second clips may each include a slot in fluid communication with the strap cavity. The strap of the respective anvil and cartridge buttresses may be threaded through the slot and into the strap cavity.

In some aspects, each of the first and second clips includes a reel rotationally supported within the strap cavity, and the strap is wound around the reel.

The first and second clips may each include a pair of fingers extending from a body of the respective first and second clips in opposed relation relative to each other.

The surgical buttress loading units are designed to guide the user into loading the anvil and cartridge buttresses quickly on the correct side of a surgical stapler in the correct orientation. Surgical buttress attachment may be designed to be quick and intuitive so that, for example, in a cartridge based system, the surgical buttresses are loaded quickly and correctly between firings so as to minimize delay or hindrance of the surgical procedure.

The surgical buttress loading units may be designed for one-handed use to allow the user to hold a surgical stapler in one hand and attach the surgical buttresses with the other hand.

In some embodiments, the anvil and cartridge buttress loading units each has a buttress cavity having a shape corresponding to the size and shape of the anvil or staple cartridge assembly of the surgical stapler upon which it is applied to aid the user in installing the surgical buttress loading unit and thus, the surgical buttresses on the correct side and in the correct orientation on the surgical stapler. The anvil assembly may have a smaller profile than the staple cartridge assembly of a surgical stapler and, in certain embodiments, the anvil buttress loading unit is loaded onto a surgical stapler prior to the cartridge buttress loading unit to ensure proper loading as the anvil buttress loading unit is too small to fit onto a staple cartridge assembly.

In some embodiments, the surgical buttress loading units are designed so that the anvil buttress loading unit has to be loaded onto a surgical stapler before the cartridge buttress loading unit. In some other embodiments, the surgical buttress loading units are designed so that the anvil and cartridge buttress loading units are loaded onto a surgical stapler at the same time. These configurations of surgical buttress loading units have a poka-yoke design thereby providing a mechanism that prevents a user for making a mistake in the process of loading the anvil and cartridge buttresses onto the surgical stapler.

BRIEF DESCRIPTION OF THE DRAWINGS

The above and other aspects, features, and advantages of the present disclosure will be apparent in light of the following detailed description when taken in conjunction with the accompanying drawings, which are incorporated in and constitute a part of this specification, wherein:

FIG. 22 is a perspective view of a surgical buttress applicator in accordance with another embodiment of the present disclosure, shown in an initial position;

FIG. 23 is a perspective view of the surgical buttress applicator of FIG. 22, shown in an actuated position;

FIG. 31 is a side view of the anvil buttress loading unit of FIG. 29, loaded with an anvil buttress and a clip;

FIG. 32 is a cross-sectional view of the clip of FIG. 31, taken along section line 32-32 of FIG. 31; and FIG. 33 is a perspective view of anvil and cartridge buttresses loaded onto a jaw assembly and an elongate tubular body portion of the surgical stapling apparatus of FIG. 1.

DETAILED DESCRIPTION

Figure 1:
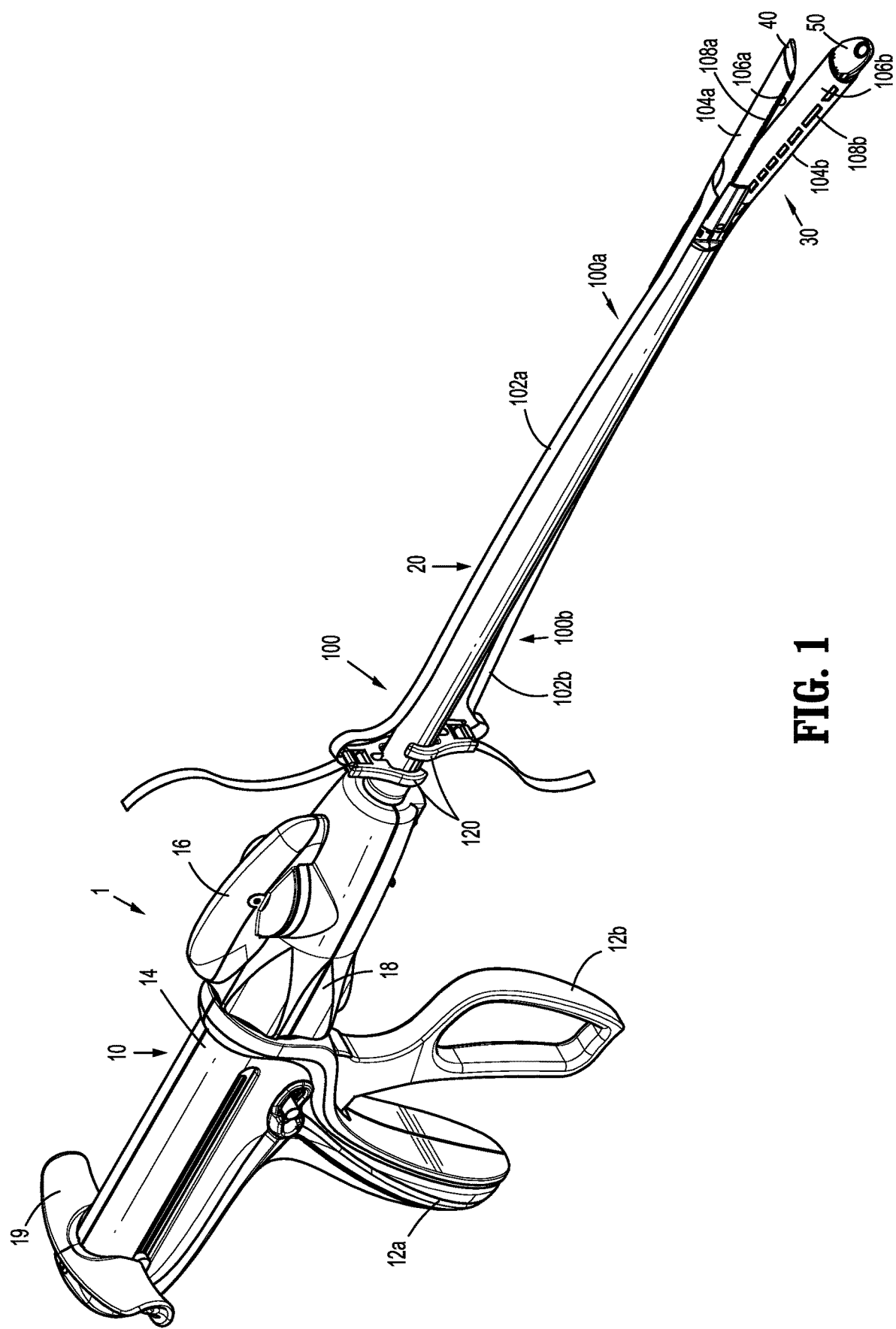
FIG. 1 is a perspective view of a surgical stapling apparatus having anvil and cartridge buttresses disposed thereon in accordance with an embodiment of the present disclosure.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to ease description of the embodiments and are not intended to have any limiting effect on the ultimate orientation of a structure or any part thereof. In the following description, well-known functions or constructions are not described in detail to avoid obscuring the present disclosure in unnecessary detail.

Referring now to FIG. 1, an exemplary surgical stapler 1 in the form of a linear surgical stapling apparatus is shown for use in stapling tissue and applying one or more buttress materials or surgical buttresses to the tissue. The surgical stapling apparatus 1 generally includes a handle assembly 10, an elongate tubular body portion 20 extending distally from the handle assembly 10, and an end effector or jaw assembly 30 extending distally from the elongate tubular body portion 20. The jaw assembly 30 includes an anvil assembly 40 and a staple cartridge assembly 50. The jaw assembly 30 may be permanently affixed to the elongate tubular body portion 20 or may be detachable with respect to the elongate tubular body portion 20 and thus, replaceable with a new jaw assembly 30. The anvil assembly 40 and/or the staple cartridge assembly 50 is pivotable with respect to the elongate tubular body portion 20 such that the anvil and/or staple cartridge assemblies 40, 50 is movable between an open position, in which the anvil and staple cartridge assemblies 40, 50 are spaced apart with respect to each other, and a closed position, in which the anvil and staple cartridge assemblies 40, 50 are substantially adjacent each other.

The handle assembly 10 includes a stationary handle member 12a, a movable handle member 12b, and a barrel portion 14. An articulation lever 16 is mounted on the forward end of the barrel portion 14 to facilitate articulation of the jaw assembly 30. A rotatable member 18 is also mounted on the forward end of the barrel portion 14, adjacent the articulation lever 16. Rotation of the rotatable member 18 relative to the barrel portion 14 rotates the elongate tubular body portion 20 and the jaw assembly 30 relative to the handle assembly 10 so as to properly orient the anvil and staple cartridge assemblies 40, 50 relative to tissue to be stapled. A knob 19 is movably positionable along the barrel portion 14. The knob 19 is advanced distally to approximate or close the anvil and staple cartridge assemblies 40, 50, relative to each other, and retracted proximally to unapproximate or open the anvil and staple cartridge assemblies 40, 50, with respect to each other. Actuation of the movable handle member 12b applies lines of staples 58 (FIG. 2) to tissue captured between the anvil and staple cartridge assemblies 40, 50.

Figure 2:
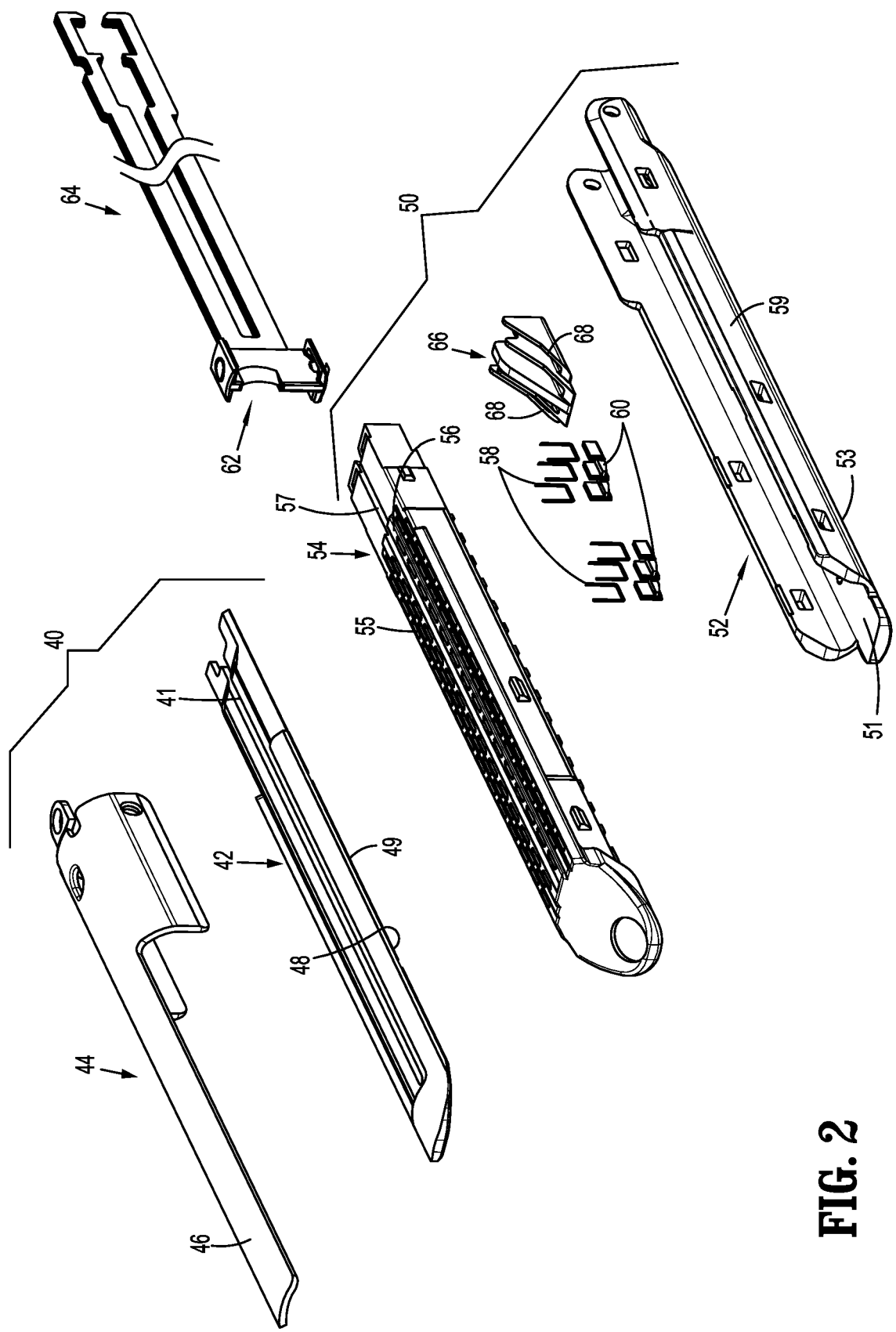
FIG. 2 is an exploded, perspective view of anvil and staple cartridge assemblies of an end effector of the surgical stapling apparatus of FIG. 1.

As shown in FIG. 2, the anvil assembly 40 includes an anvil plate 42 having a central longitudinal slot 41 formed therein, and a cover plate 44 secured over the anvil plate 42 such that the cover plate 44 defines a top or outwardly facing surface 46 of the anvil assembly 40. The anvil plate 42 may include a plurality of staple forming pockets/cavities (not shown) defined in an inwardly or tissue facing surface 48 thereof.

The staple cartridge assembly 50 includes a cartridge carrier 52 defining an elongated support channel 51 configured and dimensioned to selectively receive a staple cartridge 54 therein. The cartridge carrier 52 also defines a bottom or outwardly facing surface 53 of the staple cartridge assembly 50. The staple cartridge 54 is removable and replaceable in the cartridge carrier 52 of the staple cartridge assembly 50. The staple cartridge 54 includes an inwardly or tissue facing surface 56 defining staple pockets or retention slots 55 formed therein for receiving a plurality of fasteners or staples 58 and staple pushers 60. A central longitudinal slot 57 is formed in and extends along a substantial length of the staple cartridge 54 to facilitate passage of a knife blade 62 of a drive bar 64 therethrough. During operation of the surgical stapler 1, an actuation sled 66 translates through the staple cartridge 54 to advance cam wedges 68 of the actuation sled 66 into sequential contact with the staple pushers 60, to cause the staple pushers 60 to translate vertically within the staple pockets 55 and urge the staples 58 from the staple pockets 55 towards the tissue facing surface 48 of the anvil plate 42 of the anvil assembly 40.

For a detailed description of the structure and function of exemplary surgical stapling apparatus, reference may be made to U.S. Pat. Nos. 8,256,656, 7,819,896, and 7,128,253, the entire content of each of which is incorporated herein by reference. It should be appreciated that principles of the present disclosure are equally applicable to surgical stapling apparatus having other configurations such as, for example, the types described in U.S. Pat. Nos. 7,334,717, 5,964,394, and 5,915,616, the entire content of each of which is incorporated herein by reference. Accordingly, it should be understood that a variety of surgical stapling apparatus may be utilized with the surgical buttress loading units and associated surgical buttresses of the present disclosure such as, for example, laparoscopic staplers, open staplers, transverse anastomosis staplers, and end-to-end anastomosis staplers having a circular staple cartridge and anvil, as well as staple cartridge assemblies housing surgical fasteners other than staples.

With reference again to FIG. 1, surgical buttresses 100, shown as anvil and cartridge buttresses 100*a*, 100*b*, are releasably coupled to the anvil and staple cartridge assemblies 40, 50, respectively, of the surgical stapler 1. Each surgical buttress 100 is fabricated from biocompatible materials which are bioabsorbable or non-absorbable, natural or synthetic. It should be understood that any combination of natural, synthetic, bioabsorbable, and/or non-bioabsorbable materials may be used to form the surgical buttress 100. The surgical buttress 100 may be biodegradable (e.g., formed from bioabsorbable and bioresorable materials) such that the surgical buttress 100 decompose or is broken down (physically or chemically) under physiological conditions in the body, and the degradation products are excretable or absorbable by the body. Components or portions of the surgical buttress 100 may be formed from the same material or different materials. The entire surgical buttress 100 may be formed (e.g., cut) from a single sheet of material, or may be formed from a plurality of sheets of material, that are fabricated from the same or different materials, and attached to one another by, for example, welding, using adhesives, tying sutures, etc.

In embodiments, at least a portion of the surgical buttress 100 is made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress 100 is made from non-biodegradable materials selected from the following group: polyolefins, polyethylene, polydimethylsiloxane, polypropylene, copolymers of polyethylene and polypropylene, blends of polyethylene and polypropylene, ultra high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The surgical buttress 100 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress 100, or portions thereof, may be a non-woven structure formed by melt-blown or melt-spun methods, a mesh material, a braided material, and/or a molded or extruded sheet. The surgical buttress 100, or portions thereof, may be a single porous or non-porous layer, or include a plurality of layers including any combination of porous and/or non-porous layers.

Figure 3:
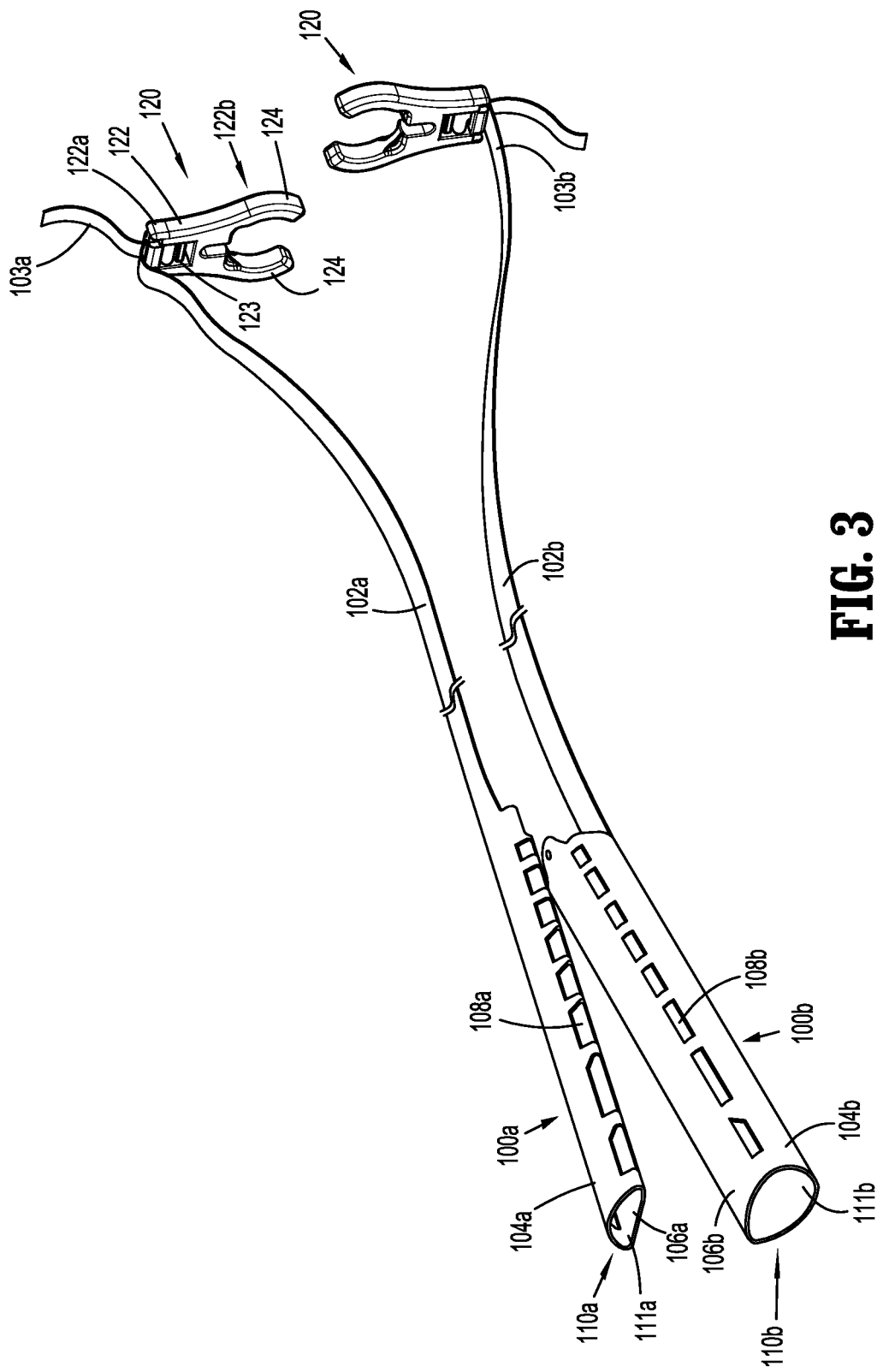
FIG. 3 is a perspective view of the anvil and cartridge buttresses of FIG. 1.

As shown in FIG. 3, the anvil and cartridge buttresses 100*a*, 100*b* each includes an elongate member or strap 102*a*, 102*b* a folded portion 104*a*, 104*b*, and a buttress portion 106*a*, 106*b*. The strap 102*a*, 102*b* is coupled to the folded portion 104*a*, 104*b*, and the folded portion 104*a*, 104*b* is coupled to the buttress portion 106*a*, 106*b* and is separable therefrom by perforations 108*a*, 108*b*. Together, the folded portion 104*a*, 104*b* and the buttress portion 106*a*, 106*b* form a tubular body 110*a*, 110*b* that is sized and shaped to facilitate the reception of the respective anvil or staple cartridge assembly 40, 50 (FIG. 1) therein. For example, as shown in FIG. 1, the anvil assembly 40 has a lower profile and is more curved in shape than the staple cartridge assembly 50, which is deeper and more rounded or more rectangular in shape. Accordingly, as seen in FIG. 3, the size and shape of the openings 111*a*, 111*b* defined in the tubular body 110*a*, 110*b* of the anvil and cartridge buttress 100*a*, 100*b* correspond with the respective anvil and staple cartridge assemblies 40, 50 (FIG. 1) onto which it is applied. Each of the openings 111*a*, 111*b* permits loading of the tubular body 110*a*, 110*b* of the anvil and cartridge buttress 100*a*, 100*b* on the designated side (e.g., anvil or staple cartridge side) in the correct orientation and direction (e.g., the buttress portion 106*a*, 106*b* abutting the respective tissue facing surface 48, 56 of the anvil or staple cartridge assembly 40, 50).

With continued reference to FIG. 3, the strap 102*a*, 102*b* is secured to the folded portion 104*a*, 104*b* of the anvil and cartridge buttress 100*a*, 100*b* and extends proximally therefrom. The strap 102*a*, 102*b* can be unitary with the folded portion 104*a*, 104*b* and/or may be permanently secured to the folded portion 104*a*, 104*b*. The strap 102*a*, 102*b* is of a sufficient length to be accessible outside of a patient's body and may extend the length of the elongate tubular body portion 20 (FIG. 1) of the surgical stapler 1. The strap 102*a*, 102*b* may be a band, a cord, a rope, a suture, among other elongate structures tethered to or integrally formed with the folded portion 104*a*, 104*b* of the anvil and cartridge buttress 100*a*, 100*b*. In some embodiments, the strap 102*a*, 102*b* may include two or more elongate sections such as, for example, a suture attached to a strip of material that extends proximally from the folded portion 104*a*, 104*b* of the anvil or cartridge buttress 100*a*, 100*b*. The strap 102*a*, 102*b* can be made from the same material, or different material, as the folded portion 104*a*, 104*b* and/or buttress portion 106*a*, 106*b*.

The folded portion 104*a*, 104*b* can include one or more sections of material, and can be made from the same material as the buttress portion 106*a*, 106*b* or from a different material, as discussed above. The folded portion 104*a*, 104*b* can be secured to itself to form the tubular body 110a, 110b and/or the buttress portion 106a, 106b can be attached to the folded portion 104a, 104b or itself. The folded portion 104a, 104b and/or the buttress portion 106a, 106b, or sections thereof, may be integrally formed or secured together via any suitable attachment features within the purview of those skilled in the art, such as, mechanical attachment features (e.g., sutures, pins), chemical attachment features (e.g., adhesives), and/or attachment methods (e.g., welding).

The perforations 108a, 108b are disposed between the folded portion 104a, 104b and the buttress portion 106a, 106b of the respective anvil and cartridge buttress 100a, 100b, and are optimized to allow for sequential detachment of the folded portion 104a, 104b from the buttress portion 106a, 106b when the strap 102a, 102b is pulled. The perforations 108a, 108b can be any size and shape, such as small pin-holes or larger openings such as, for example, the elongated openings shown in FIG. 3, or the perforations 108a, 108b can be a single feature, such as a line of weakness in the buttress material or materials forming the folded portion 104a, 104b and the buttress portion 106a, 106b. The perforations 108a, 108b may be formed using laser cutting, knife cutting, press cutting, scoring, etching, among other methods within the purview of those skilled in the art.

When the strap 102a, 102b is pulled away from the tubular body 110a, 110b (e.g., proximally towards a user), the folded portion 104a, 104b and the strap 102a, 102b separate from the buttress portion 106a, 106b along the perforations 108a, 108b. It should be understood, however, that the perforations 108a, 108b may be omitted from the anvil and cartridge buttress 100a, 100b. For example, the juncture between the folded portion 104a, 104b and the buttress portion 106a, 106b may be formed or otherwise secured to one another to facilitate separation of the folded portion 104a, 104b from the buttress portion 106a, 106b upon application of a force to the strap 102a, 102b.

A clip 120 is secured to a proximal end portion 103a, 103b of the strap 102a, 102b. The clip 120 includes a body 122 having a first end portion 122a including at least one opening 123 through which the strap 102a, 102b may be threaded for attachment thereto, and a second end portion 122b including a pair of fingers 124 extending therefrom in opposed relation relative to each other. The pair of fingers 124 are substantially c-shaped or u-shaped and are configured to engage the elongate tubular body portion 20 (FIG. 1) of the surgical stapler 1 to securely, yet releasably fasten the clip 120 and thus, the strap 102a, 102b of the anvil and cartridge buttress 100a, 100b to the surgical stapler 1. It is envisioned that the proximal end portion 103a, 103b of the strap 102a, 102b may be secured to the clip 120 or the elongate tubular body portion 20 of the surgical stapler 1 in other ways and/or other modifications may be made to the clip 120 for securing the same to the surgical stapler 1.

The clip 120 may include a boss 126 (FIG. 5) extending from the body 122 for releasably engaging a surgical buttress applicator or a surgical buttress loading unit, as described in further detail below. The boss 126 may be a cylindrical projection or protuberance that can engage an opening or recess of the surgical buttress application. The boss 126 may extend from any portion of the clip 120 depending, for example, on the desired retaining position of the clip 120 relative to the surgical buttress applicator or surgical buttress loading unit.

With continued reference to FIGS. 1-3, the anvil and cartridge buttresses 100a, 100b are disposed on the anvil and staple cartridge assemblies 40, 50 of the surgical stapler 1 with the buttress portion 106a, 106b positioned over the respective tissue facing surface 48, 56 of the anvil or staple cartridge assembly 40, 50, the folded portion 104a, 104b positioned over the respective outwardly facing surface 46, 53 of the anvil or staple cartridge assembly 40, 50, and the strap 102a, 102b extending proximally along the elongate tubular body portion 20 of the surgical stapler 1 and secured thereto via the clips 120. The perforations 108a, 108b are positioned adjacent respective side surfaces 49, 59 of the anvil or staple cartridge assembly 40, 50.

Figure 4:
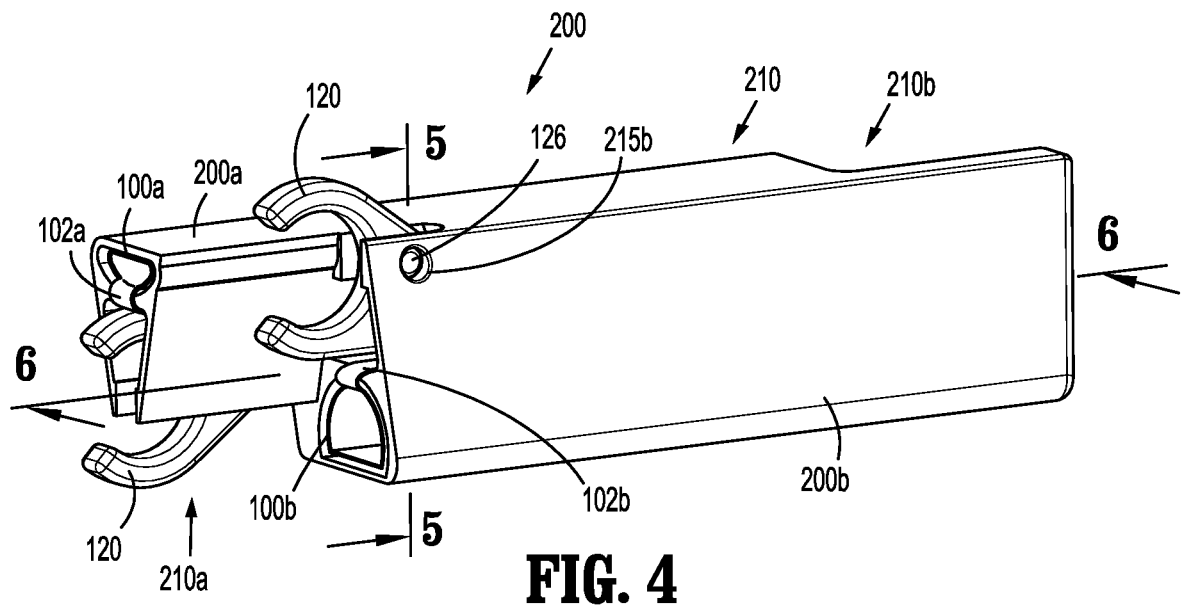
FIG. 4 is a perspective view of a surgical buttress applicator in accordance with an embodiment of the present disclosure, including the anvil and cartridge buttresses of FIG. 1 loaded therein.

Turning now to FIG. 4, a surgical buttress applicator or assembly 200 is shown. The surgical buttress applicator 200 is configured for positioning the anvil and cartridge buttresses 100a, 100b onto a surgical stapler 1 (FIG. 1). The surgical buttress applicator 200 includes a body 210 having an anvil buttress loading side or unit 200a and a cartridge buttress loading side or unit 200b.

Figure 5:
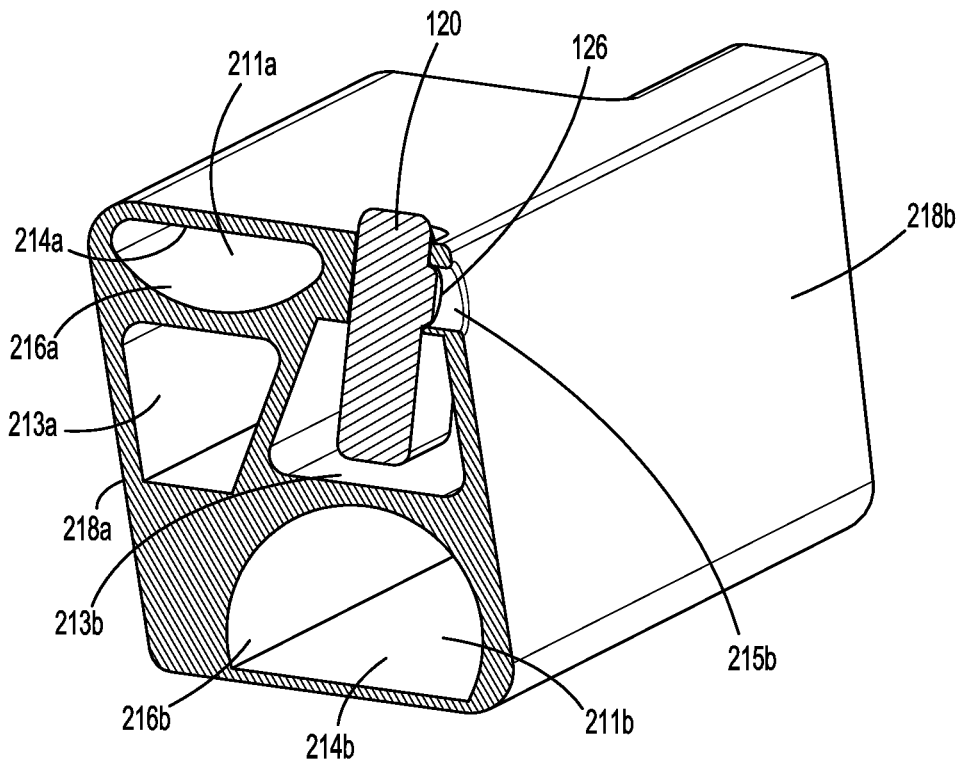
FIG. 5 is a cross-sectional view of the surgical buttress applicator of FIG. 4, taken along section line 5-5 of FIG. 4, with the anvil and cartridge buttresses removed therefrom.
Figure 6:
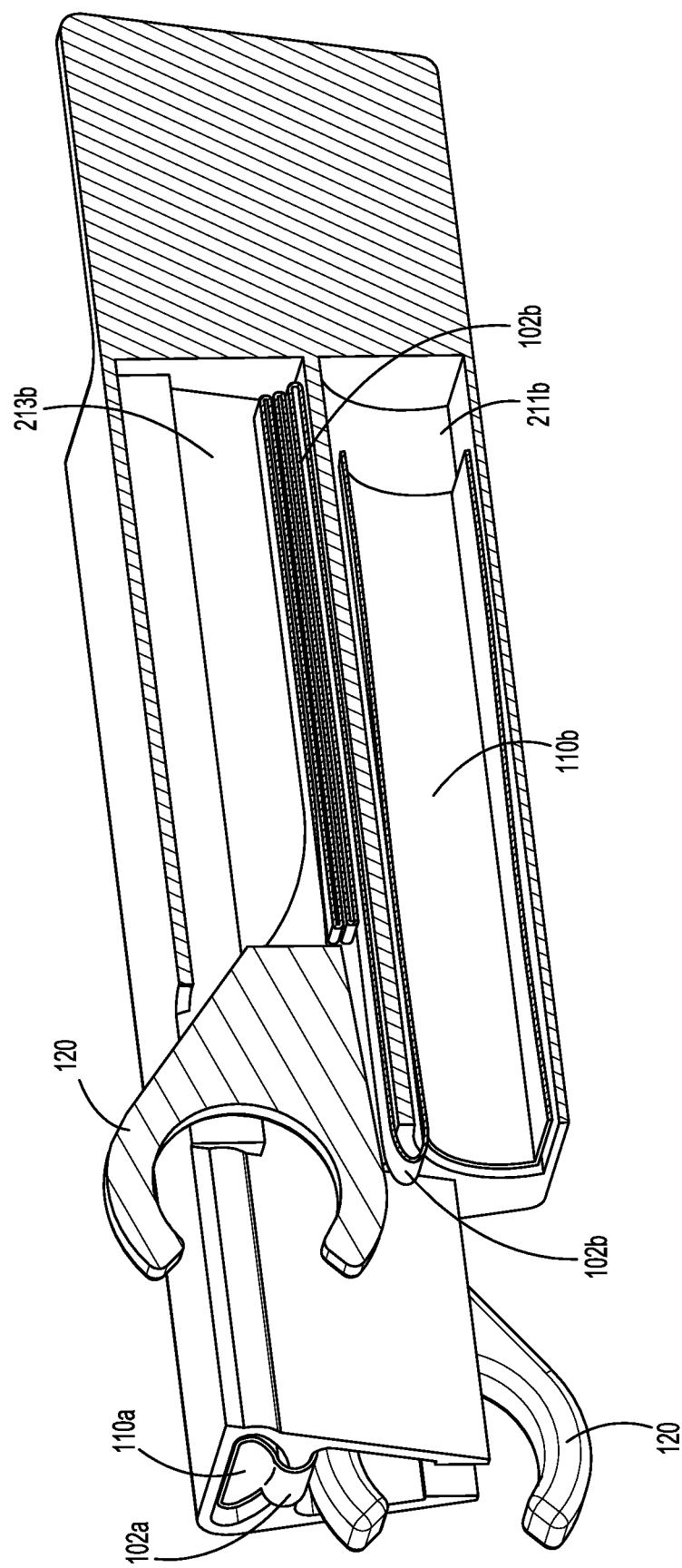
FIG. 6 is a cross-sectional view of the surgical buttress applicator of FIG. 4, taken along section line 6-6 of FIG. 4.

As shown in FIGS. 4-6, the anvil buttress loading side 200a of the body 210 of the surgical buttress applicator 200 includes a buttress cavity 211a and a strap cavity 213a, and the cartridge buttress loading side 200b includes a buttress cavity 211b and a strap cavity 213b. The buttress cavities 211a, 211b are configured to retain the tubular bodies 110a, 110b of the respective anvil and cartridge buttresses 100a, 100b therein, and the strap cavities 213a, 213b are configured to retain the straps 102a, 102b, as well as at least a portion of the clips 120, of the respective anvil and cartridge buttresses 100a, 100b therein.

The buttress cavities 211a, 211b each includes a first or substantially flat wall section 214a, 214b corresponding to the tissue facing surface 48, 56 (FIG. 2) of the anvil or staple cartridge assembly 40, 50, and a second or rounded wall section 216a, 216b configured to extend around the anvil or staple cartridge assembly 40, 50 and over the outwardly facing surface 46, 53 (FIG. 2) of the anvil or staple cartridge assembly 40, 50. The configuration of the buttress cavities 211a, 211b allow the tubular bodies 110a, 110b of the anvil and cartridge buttresses 100a, 100b to be retained therein in an open configuration for slidably receiving the anvil or staple cartridge assembly 40, 50 (FIG. 1) therein.

The strap cavities 213a, 213b each includes an opening 215a, 215b defined in a lateral side or side wall 218a, 218b of the body 210 of the surgical buttress applicator 200. The opening 215a, 215b is releasably engageable with the boss 126 of the clip 120 for retaining the clip 120 thereto.

The body 210 of the surgical buttress applicator 200 includes a proximal end 210a and a distal end 210b. The proximal end 210a is a substantially stepped surface defining openings into the buttress cavities 211a, 211b and the strap cavities 213a, 213b, where the buttress and strap cavities 211a, 213a of the anvil buttress loading side 200a is disposed proximal of the buttress and strap cavities 211b, 213b of the cartridge buttress loading side 200b. The distal end 210b of the body 210 is closed. It is envisioned, however, that the distal end 210b of the body 210 may be open.

In a method of loading the anvil and cartridge buttresses 100a, 100b into the surgical buttress applicator 200, the tubular body 110a of the anvil buttress 100a is positioned in the buttress cavity 211a of the anvil buttress loading side 200a with the folded portion 104a of the anvil buttress 100a positioned adjacent the second wall section 216a of the body 210 and the buttress portion 106a disposed adjacent to the first wall section 214a of the body 210 such that the tubular body 110a is open to receive the anvil assembly 40 (FIG. 1) of the surgical stapler 1 therein. The strap 102a of the anvil buttress 100a extends out of the buttress cavity 211a (through the opening in the proximal end 210a of the body 210) and into the strap cavity 213a. The strap 102a is folded upon itself (or otherwise retained) within the strap cavity 213a and the clip 120 is partially retained within the strap cavity 213a by engaging the boss 126 of the clip 120 with the opening 215a defined through the lateral side 218a of the body 210 of the surgical buttress applicator 200.

The tubular body 110b of the cartridge buttress 100b is positioned in the buttress cavity 211b of the cartridge buttress loading side 200b with the folded portion 104b of the cartridge buttress 100b positioned adjacent the second wall section 216b of the body 210 and the buttress portion 106b disposed adjacent to the first wall section 214b of the body 210 such that the tubular body 110b is open to receive the staple cartridge assembly 50 (FIG. 1) of the surgical stapler 1 therein. The strap 102b of the cartridge buttress 100b extends out of the buttress cavity 211b (through the opening in the proximal end 210b of the body 210) and into the strap cavity 213b. As seen in FIG. 6, the strap 102b is folded upon itself within the strap cavity 213b and the clip 120 is partially retained within the strap cavity 213b by engaging the boss 126 (FIG. 5) of the clip 120 with the opening 215b defined through the lateral side 218b of the body 210 of the surgical buttress applicator 200.

Figure 7:
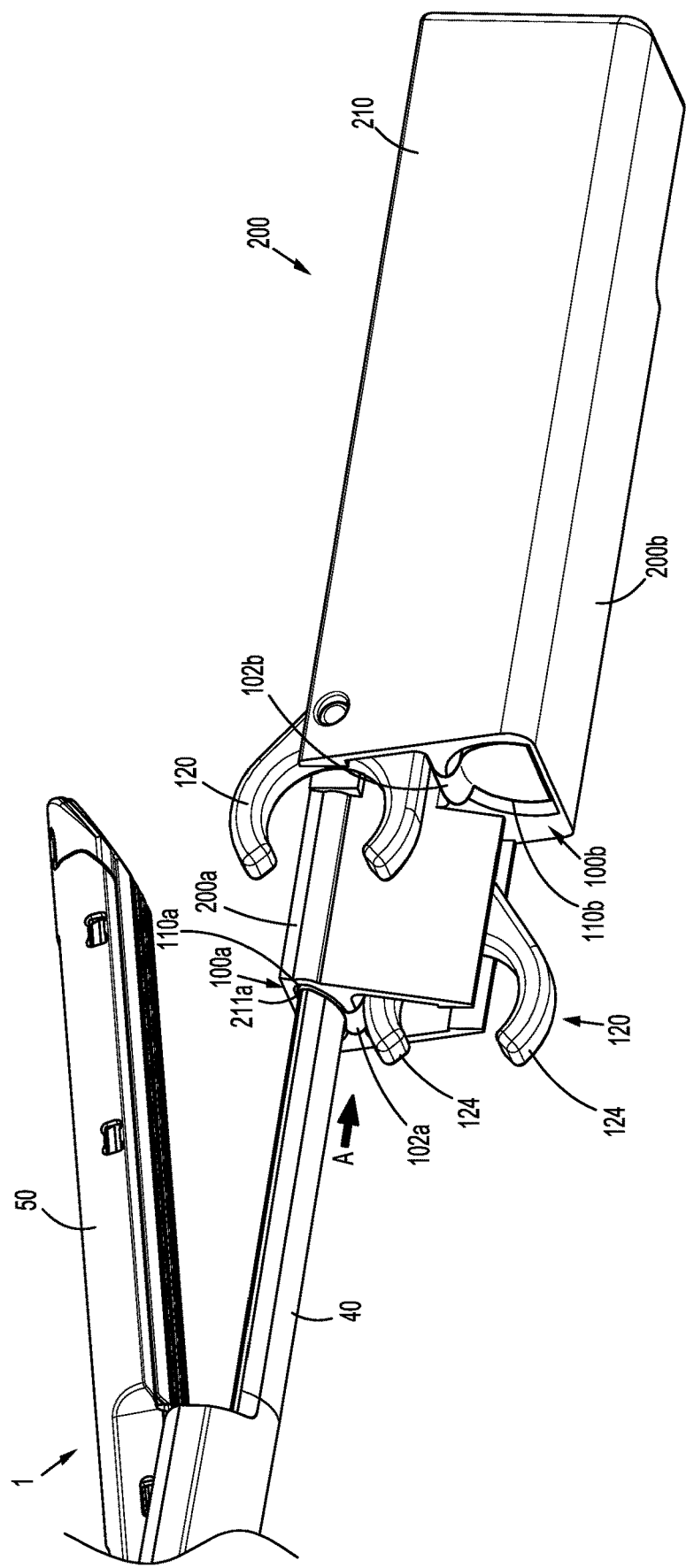
FIG. 7 is a perspective view of an anvil assembly of the surgical stapling apparatus of FIG. 1 being inserted into the surgical buttress applicator of FIG. 4.

In a method of loading the anvil and cartridge buttresses 100a, 100b onto the surgical stapler 1, the surgical buttress applicator 200 is first applied to the anvil assembly 40 of the surgical stapler 1. A user grasps the body 210 of the surgical buttress applicator 200 and manipulate the surgical buttress applicator 200 onto the anvil assembly 40 by aligning the buttress cavity 211a of the anvil buttress loading side 200a with the distal end of the anvil assembly 40, as shown in FIG. 7, and sliding the anvil assembly 40 into the surgical buttress applicator 200, in the direction of arrow "A," until the anvil assembly 40 is positioned within the buttress cavity 211a and/or forward motion of the anvil assembly 40 relative to the surgical buttress applicator 200 is prohibited.

With the surgical buttress applicator 200 applied onto the anvil assembly 40 such that the anvil assembly 40 is received within the tubular body 110a of the anvil buttress 100a, the clip 120 of the anvil buttress 100a is detached from the body 210 of the surgical buttress applicator 200 and pulled proximally towards the user thereby unfurling the strap 102a from the strap cavity 213a. The clip 120 is secured to the elongate tubular body portion 20 (FIG. 1) of the surgical stapler 1 by engaging the pair of fingers 124 with the elongate tubular body portion 20 at a position proximal of the end effector 30, such as adjacent to the handle assembly 10 (FIG. 1) of the surgical stapler 1, and/or at least at a location outside of a patient's body during a surgical procedure. The user can then grasp the body 210 of the surgical buttress applicator 200 and slide it distally off of the anvil assembly 40. The surgical buttress applicator 200 may be removed from the anvil assembly 40 either prior to, or after, attaching the clip 120 to the surgical stapler 1. As the surgical buttress applicator 200 is slid away from the surgical stapler 1, the anvil buttress 100a disengages from the body 210 and is retained on the anvil assembly 40 such that the anvil buttress 100a is left loaded on the anvil assembly 40, as shown, for example, in FIG. 1.

The cartridge assembly 50 is then loaded in a similar manner. The user grasps the body 210 of the surgical buttress applicator 200 and manipulates the surgical buttress applicator 200 onto the cartridge assembly 50 by aligning the buttress cavity 211b on the cartridge buttress loading side 200b with the distal end of the cartridge assembly 50 and sliding the surgical buttress applicator 200 over the cartridge assembly 50 until the cartridge assembly 50 is received within the buttress cavity 211b and thus, the tubular body 110b of the cartridge buttress 100b. The clip 120 is then detached from the body 210 and pulled proximally towards the user thereby unfurling the strap 102b from the strap cavity 213b. The clip 120 is secured to the elongate tubular body portion 20 of the surgical stapler 1, as described above with respect to the clip 120 of the anvil buttress 100a, and then the body 210 of the surgical buttress applicator 200 is slid distally off of the cartridge assembly 50. As the surgical buttress applicator 200 is slid away from the surgical stapler 1, the cartridge buttress 100b disengages the body 210 and is retained on the cartridge assembly 50 such that the cartridge buttress 100b is left loaded on the cartridge assembly 50. The surgical stapler 1, loaded with the anvil and cartridge buttresses 100a, 100b, as shown in FIG. 1, is now ready for use.

The anvil buttress loading side 200a of the surgical buttress applicator 200 is disposed proximal of the cartridge buttress loading side 200b such that the anvil assembly 40 is loaded first. With the anvil buttress loading side 200a presented first (e.g., in front of the cartridge buttress loading side 200b), a user intuitively loads this first presented loading side. As the buttress cavity 211a of the anvil buttress loading side 200a is physically smaller than the buttress cavity 211b of the cartridge buttress loading side 200b, only the anvil assembly 40 of the surgical stapler 1 may engage the anvil buttress loading side 200a in the proper orientation. Accordingly, after the anvil assembly 40 is loaded, the staple cartridge assembly 50, by default, will be loaded correctly.

In a method of use, the loaded surgical stapler 1 is introduced to a surgical site through a trocar or other access device. The surgical stapler 1 is operated within methods known by those skilled in the art. Once the anvil and staple cartridge assemblies 40, 50 are clamped onto tissue, the surgical stapler 1 is fired. In firing the surgical stapler 1, the drive bar 64 (FIG. 2) is advanced distally through the jaw assembly 30 urging the staple pushers 60 upwardly which, in turn, drive the staples 58 out of the staple pockets 55 and through the buttress portions 106a, 106b of the anvil and cartridge buttresses 100a, 100b as well as the captured tissue, thereby stapling the buttress portions 106a, 106b to the tissue. During firing, the knife blade 62 of the drive bar 64 travels distally while substantially simultaneously cutting and dividing the tissue as well as the buttress portions 106 of the anvil and cartridge buttresses 100a, 100b disposed between the rows of now formed staples 58.

The folded portions 104a, 104b and the straps 102a, 102b of the anvil and cartridge buttresses 100a, 100b can then be detached from the now-stapled buttress portions 106a, 106b by pulling the handle assembly 10 and thus, the surgical stapler 1, proximally to tear the folded portion 104a, 104b from the buttress portion 106a, 106b via the perforations 108a, 108b as the clips 120 are attached to the surgical stapler 1. Additionally or alternatively, the folded portion 104a, 104b may be pulled by the user by grasping an exposed portion of the strap 102a, 102b or the clip 120 and pulling the strap 102a, 102b and/or the clip 120 directly. Accordingly, the folded portion 104a, 104b and the straps 102a, 102b may be removed from the surgical site either during removal of the surgical stapler 1 therefrom or by separate removal.

Figure 8:
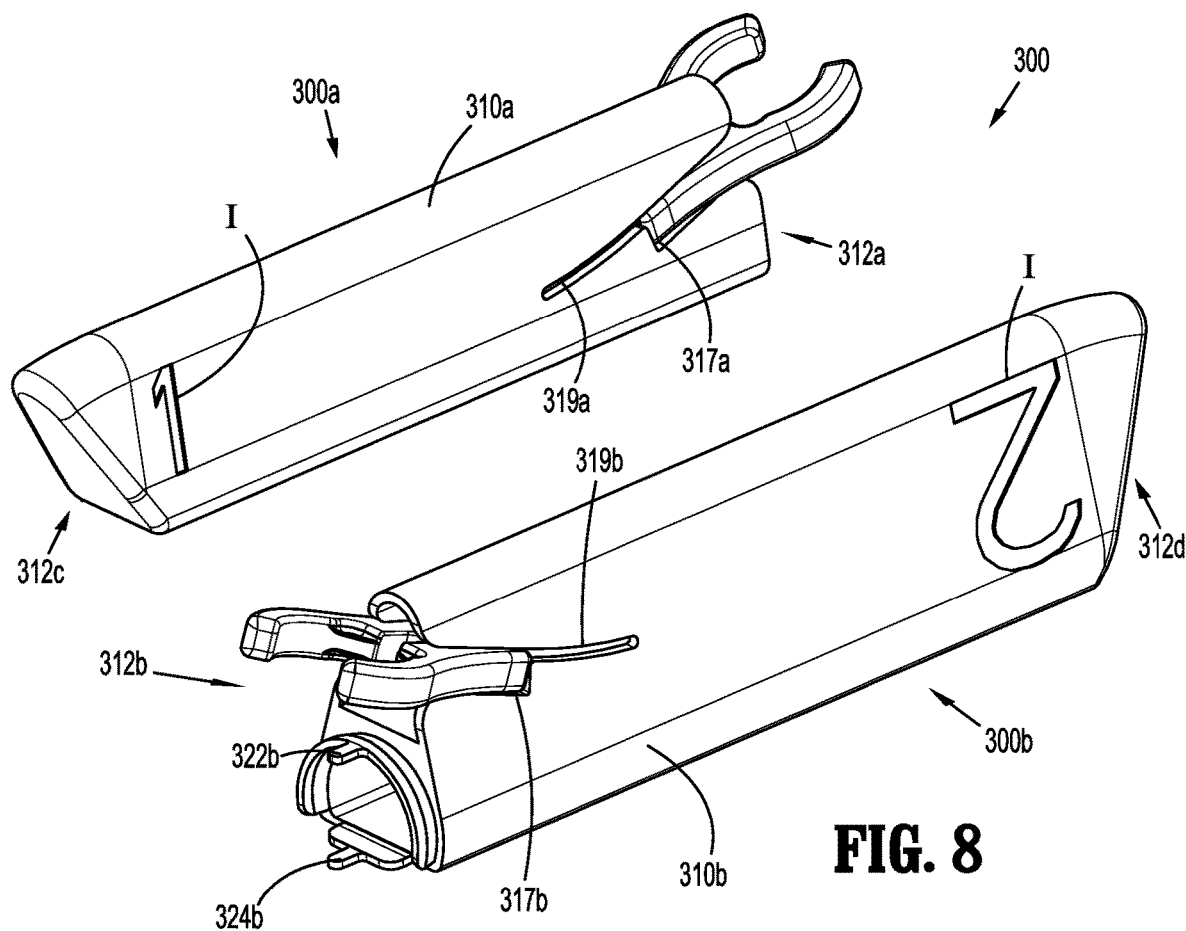
FIG. 8 is a perspective view of a surgical buttress applicator in accordance with another embodiment of the present disclosure.
Figure 9:
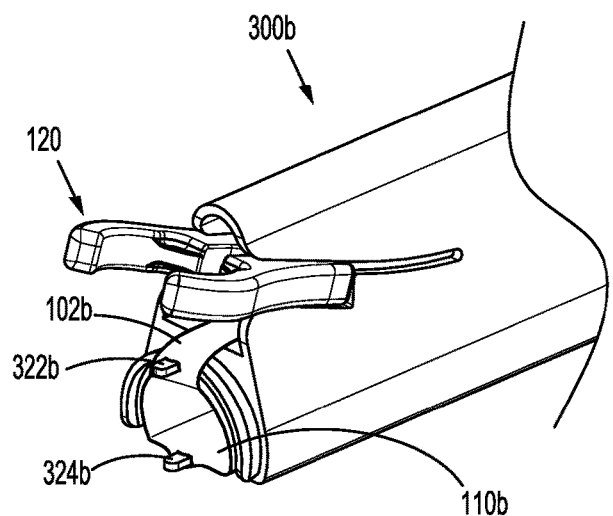
FIG. 9 is a close-up view of a cartridge buttress loading unit of the surgical buttress applicator of FIG. 8, loaded with a cartridge buttress.
Figure 10:
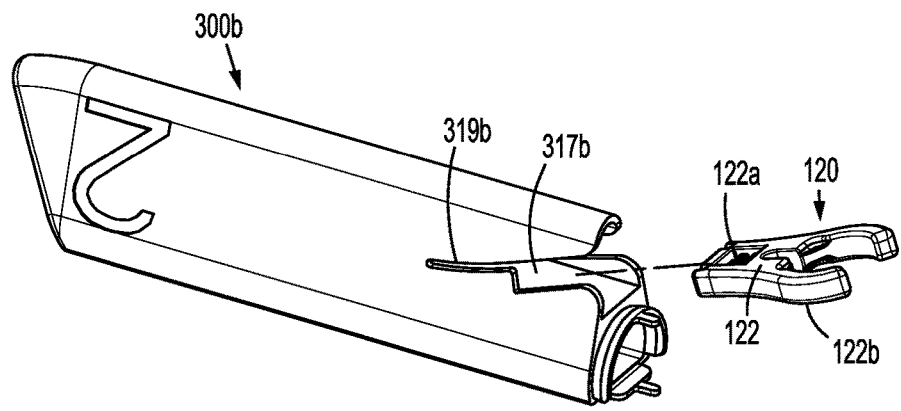
FIG. 10 is a perspective view of the cartridge buttress loading unit of FIG. 9.

With reference now to FIG. 8, a surgical buttress applicator 300 includes an anvil buttress loading unit 300a and a cartridge buttress loading unit 300b. The anvil and cartridge buttress loading units 300a, 300b are separate units and are labeled with indicia "I," shown, for example, as "1" and "2,"

respectively. It should be understood, however, that other indicia for indicating loading order/sequence onto a surgical stapler may be utilized.

As shown in FIGS. 8-11, the anvil and cartridge buttress loading units 300a, 300b each includes a body 310a, 310b having a proximal end 312a, 312b and a distal end 312c, 312d, and each defines a buttress cavity 311a, 311b and a strap cavity 313a, 313b therein. The buttress cavity 311a, 311b is sized and shaped, as described above with respect to buttress cavities 211a, 211b of surgical buttress applicator 200, to retain the tubular body 110a, 110b of the anvil or cartridge buttress 100a, 100b therein in an open configuration, and to further, slidably receive the respective anvil or staple cartridge assembly 40, 50 (FIG. 1) of the surgical stapler 1 therein. The buttress cavities 311a, 311b each includes a first or substantially flat wall section 314a, 314b corresponding to the tissue facing surface 48, 56 (FIG. 2) of the anvil or staple cartridge assembly 40, 50, and a second or rounded wall section 316a, 316b configured to extend around the anvil or staple cartridge assembly 40, 50 and over the outwardly facing surface 46, 53 (FIG. 2) of the anvil or staple cartridge assembly 40, 50.

The proximal end 312a of the anvil buttress loading unit 300a further includes first and second tabs 322a, 324a extending proximally and axially from the respective first and second wall sections 314a, 316a of the buttress cavity 311a in opposed relation relative to each other. The first and second tabs 322a, 324a are configured to engage the anvil buttress 100a and aid in retaining the tubular body 110a in an open configuration within the buttress cavity 311a. Likewise, the proximal end 312b of the cartridge buttress loading unit 300b includes first and second tabs 322b, 324b extending proximally and axially from the respective first and second wall sections 314b, 316b of the buttress cavity 311b in opposed relation relative to each other, and are configured to engage the cartridge buttress 100b and aid in retaining the tubular body 110b in an open configuration within the buttress cavity 311b.

The strap cavity 313a, 313b is configured to retain the strap 102a, 102b, as well as at least a portion of the clip 120, of the respective anvil and cartridge buttress 100a, 100b therein. The strap cavities 313a, 313b each includes a cutout 317a, 317b at the proximal end of the body 310 releasably engageable with the clip 120 (the first end portion 122a of the clip 120 is disposed within the cutout 317a, 317b and the second end portion 122b is exposed and extends outwardly therefrom). A slit 319a, 319b extends distally from the cutout 317a, 317b to allow for flexure of the body 310a, 310b such that the body 310a, 310b can grip or frictionally engage the clip 120 when the clip 120 is positioned within the cutout 317a, 317b.

The anvil and cartridge buttresses 100a, 100b are loaded into the surgical buttress applicator 300 in a similar manner as described above with respect to the surgical buttress applicator 200. Specifically, the tubular bodies 110a, 110b of the anvil and cartridge buttresses 100a, 100b are positioned in the respective buttress cavity 311a, 311b such that the tubular bodies 110a, 110b are open to receive the anvil and staple cartridge assemblies 40, 50 (FIG. 1) of the surgical stapler 1 therein. The straps 102a, 102b extend out of the buttress cavities 311a, 311b (through the opening in the proximal end 312a, 312b of the body 310a, 310b) and into the strap cavities 313a, 313b. The straps 102a, 102b are folded, or otherwise retained, within the strap cavities 313a, 313b and the clips 120 are partially retained within the strap cavity 313a, 313b by positioning the first end portions 122a of the clips 120 within the strap cavities 313a, 313b and engaging the bodies 122 of the clips 120 with the cutouts 317a, 317b.

Further, the anvil and cartridge buttresses 100a, 100b are engaged with the first tabs 322a, 322b and the second tabs 324a, 324b of the respective buttress cavities 311a, 311b. Specifically, the portion of the strap 102a, 102b extending from the tubular body 110a, 110b and out of the buttress cavity 311a, 311b is secured to the first tab 322a, 322b of the surgical buttress applicator 300 to help retain the tubular body 110a, 110b within the body 310a, 310b in the open configuration. The first tab 322a, 322b may be positioned through an aperture (not explicitly shown) defined through the strap 102a, 102b. The aperture may be pre-formed in the anvil or cartridge buttress 100a, 100b, or the aperture may formed during assembly of the anvil or cartridge buttress 100a, 100b into the surgical buttress applicator 300. The second tab 324a, 324b of the body 310a, 310b of the surgical buttress applicator 300 may be engaged with an aperture (not explicitly shown) defined in the buttress portion 106a, 106b of the anvil and cartridge buttress 100a, 100b to further help retain the tubular body 110a, 110b of the anvil and cartridge buttress 100a, 100b within the body 310a, 310b of the anvil or cartridge buttress loading unit 300a, 300b in the open configuration for receiving the anvil and staple cartridge assembly 40, 50 of the surgical stapler 1 therein.

In a method of loading the anvil and cartridge buttresses 100a, 100b onto the surgical stapler 1, a user grasps the anvil buttress loading unit 300a, labeled "1," and aligns the buttress cavity 311a of the anvil buttress loading unit 300a with the distal end of the anvil assembly 40 and slides the anvil buttress loading unit 300a over the anvil assembly 40 (or the anvil assembly 40 into the anvil buttress loading unit 300a or both). The clip 120 is then detached from the anvil buttress loading unit 300a and is pulled proximally towards the user (e.g., towards the handle assembly 110 of the surgical stapler 1 or generally away from the anvil buttress loading unit 300a such that the strap 102a is unfurled from the strap cavity 313a of the anvil buttress loading unit 300a) and the clip 120 is attached to the elongate tubular body portion 20 of the surgical stapler 1. The anvil buttress loading unit 300a can then be removed from the anvil assembly 40. As the anvil buttress loading unit 300a is moved away from the anvil assembly 40, the anvil buttress 100a disengages from the first and second tabs 322a, 324a of the body 310a of the anvil buttress loading unit 300a and the tubular body 110a frees from the buttress cavity 311a such that the anvil buttress 100a is left loaded on the anvil assembly 40 of the surgical stapler 1.

The staple cartridge assembly 50 is then loaded in a similar manner. The user grasps the cartridge buttress loading unit 300b of the surgical buttress applicator 300, labeled "2," and aligns the buttress cavity 311b with the distal end of the cartridge assembly 50 and slides the cartridge buttress loading unit 300b over the staple cartridge assembly 50 until the staple cartridge assembly 50 is fully received within the buttress cavity 311b and thus, the tubular body 110b of the cartridge buttress 100b. The clip 120 is then detached from the body 310b and pulled proximally towards the user thereby unfurling the strap 102b from the strap cavity 313b. The clip 120 is secured to the elongate tubular body portion 20 of the surgical stapler 1, as described above with respect to the clip 120 of the anvil buttress 100a, and then the body 310a of the cartridge buttress loading unit 300b is slid off of the staple cartridge assembly 50. As the body 310b is moved away from the staple cartridge assembly 50, the cartridge buttress 100b disengages from the first and second tabs 322*b*, 324*b* of the body 310*b* of the cartridge buttress loading unit 300*b* and the tubular body 110*b* frees from the buttress cavity 311*b* such that the cartridge buttress 100*b* is left loaded on the staple cartridge assembly 50 of the surgical stapler 1. The surgical stapler 1, loaded with the anvil and cartridge buttresses 100*a*, 100*b*, is now ready for use. The loaded surgical stapler 1 is used, for example, as discussed above with regard to surgical buttress applicator 200.

Labeling of the anvil and cartridge buttress loading units 300*a*, 300*b* with indicia "I" tells the user which loading unit to assemble onto the surgical stapler 1 first (e.g., order of loading). For example, the labeling of the anvil buttress loading unit 300*a* as "1" indicates that the anvil assembly 40 is loaded first as only the anvil assembly 40 fits into the anvil buttress loading unit 300*a*. Accordingly, after the anvil assembly 40 is loaded, the staple cartridge assembly 50, by default, should be loaded correctly.

Figure 12:
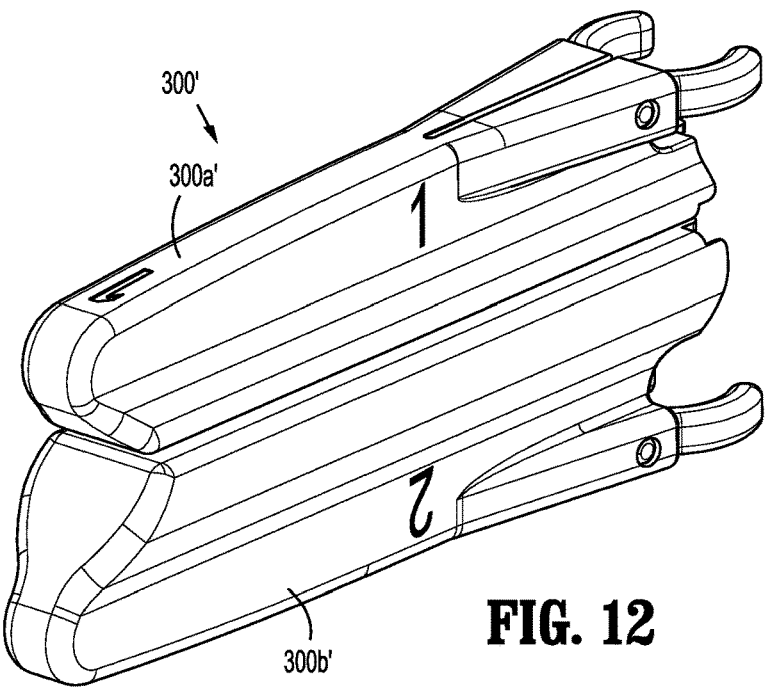
FIGS. 12 and 13 are perspective views of a surgical buttress applicator in accordance with another embodiment of the present disclosure.
Figure 13:
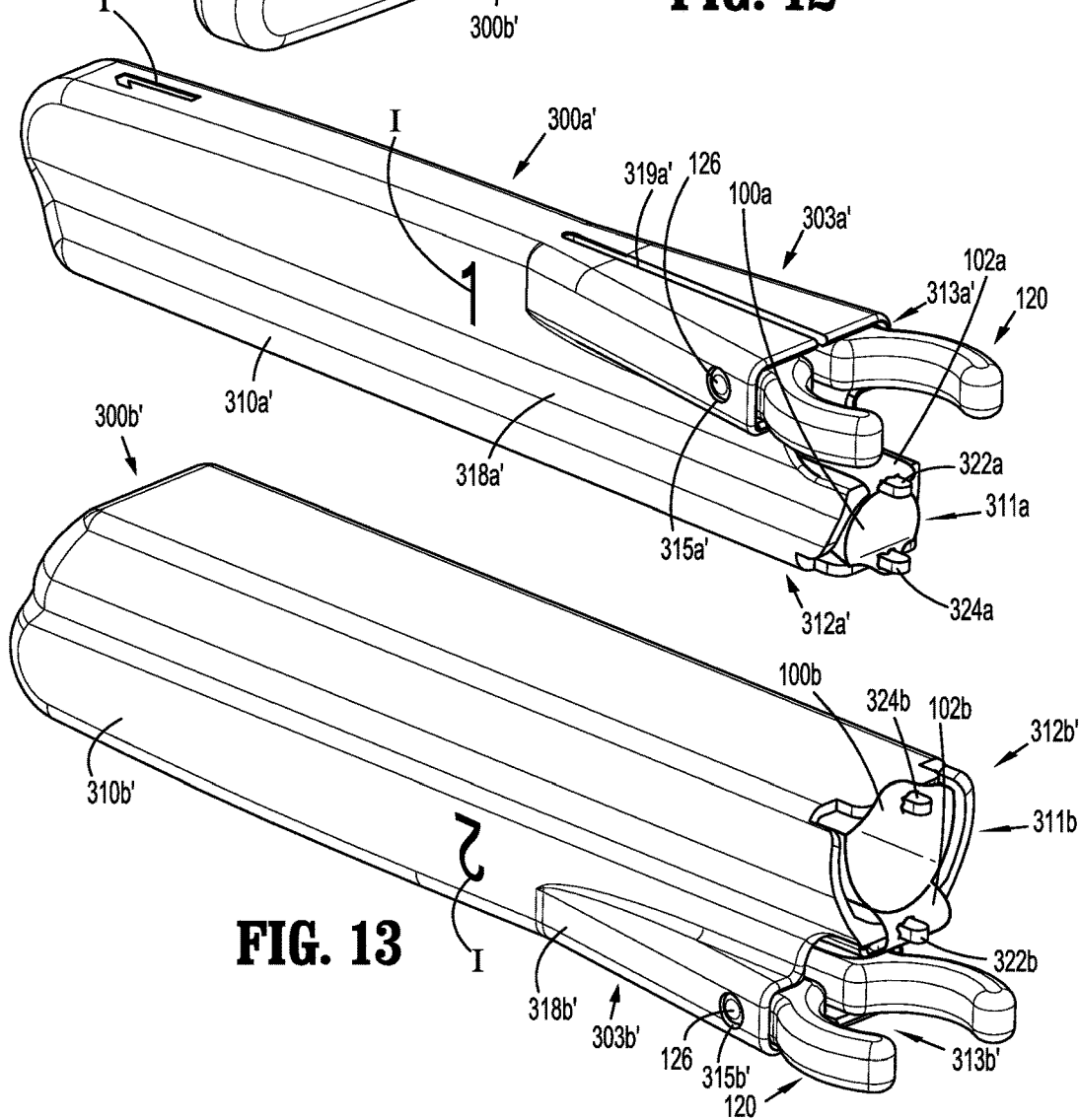

The configuration of the anvil and cartridge buttress loading units 300*a*, 300*b* may vary. For example, as shown in FIGS. 12 and 13, a surgical buttress applicator 300' includes anvil and cartridge buttress loading units 300*a*', 300*b*'. Indicia "I" is provided on the body 310*a*', 310*b*' of the anvil and cartridge buttress loading units 300*a*', 300*b*' to indicate proper loading onto a surgical stapler. The anvil and cartridge buttress loading units 300*a*', 300*b*' each has a buttress cavity 311*a*, 311*b* including a first tab 322*a*, 322*b* and a second tab 324*a*, 324*b* extending proximally therefrom, and a strap cavity 313*a*', 313*b*'. A proximal end portion 303*a*', 303*b*' of the strap cavity 313*a*', 313*b*' widens proximally towards the proximal end 312*a*', 312*b*' of the body 310*a*', 310*b*' of the anvil and cartridge buttress loading units 300*a*', 300*b*' for retaining portions of the clips 120 therein. A slit 319*a*', 319*b*' extends through the proximal end portion 303*a*', 303*b*' of the strap cavity 313*a*', 313*b*' to allow the proximal end portion 303*a*', 303*b*' to flex and grip the clip 120 when the clip 120 is positioned therein. The first end portion 122*a* and the body 122 of the clip 120 are configured for positioning in the proximal end portion 303*a*', 303*b*' of the strap cavity 313*a*', 313*b*'. The strap cavity 313*a*', 313*b*' further includes an opening 315*a*', 315*b*' in the lateral side 318*a*, 318*b* of the body 310*a*', 310*b*' to accommodate the boss 126 of the clip 120.

Figure 11:
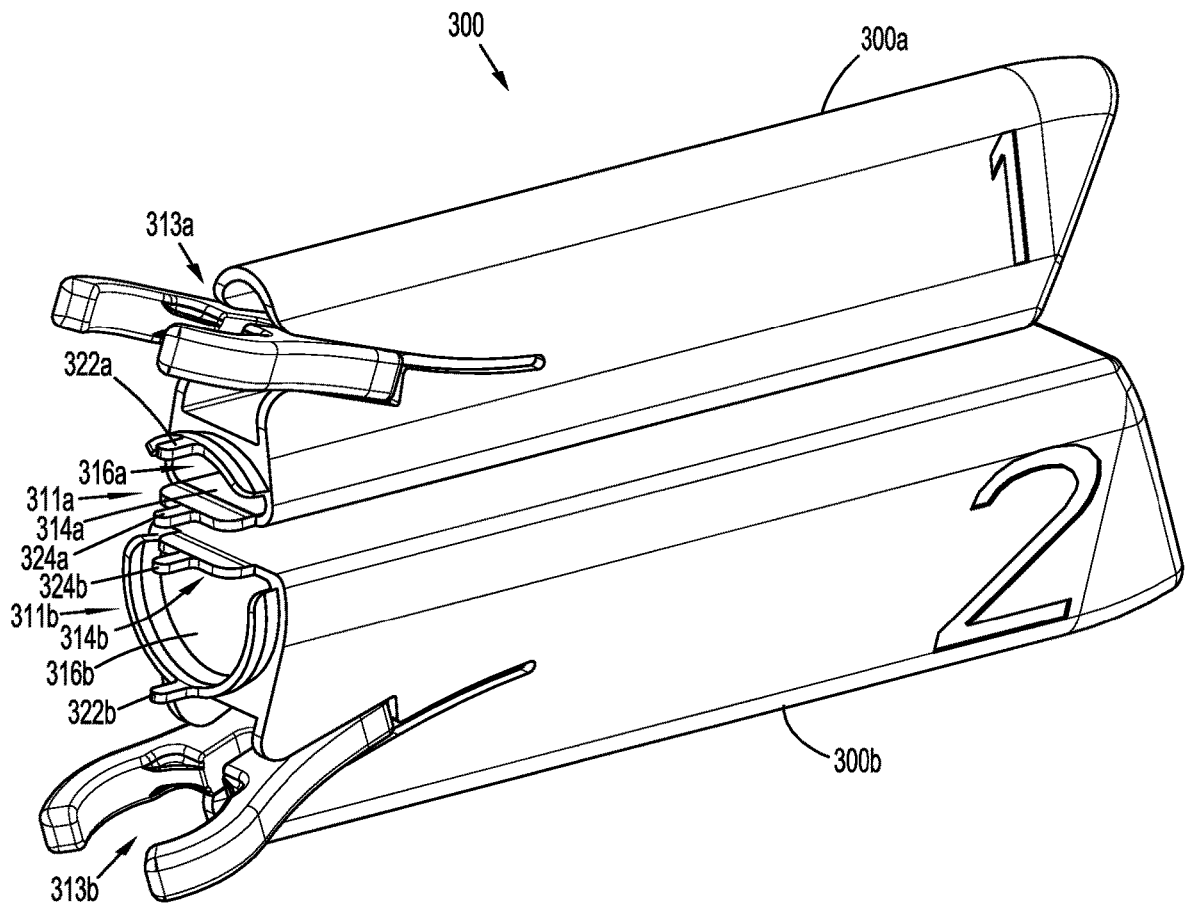
FIG. 11 is a perspective view of the surgical buttress applicator of FIG. 8.

Further, as seen, for example, in FIGS. 11 and 12, the anvil buttress loading units 300*a*, 300*a*' and cartridge buttress loading units 300*b*, 300*b*' may each include complementary surfaces (e.g., flat surfaces) which may be joined together (e.g., adhered, welded, etc.) such that the buttress cavities 311*a*, 311*b* are oriented and/or aligned so that the anvil and staple cartridge assemblies 40, 50 can be loaded at the same time and/or the surgical buttress applicator 300, 300' does not have to be manipulated (e.g., turned, etc.) during separate loading of each of the anvil and staple cartridge assemblies 40, 50.

Figure 14:
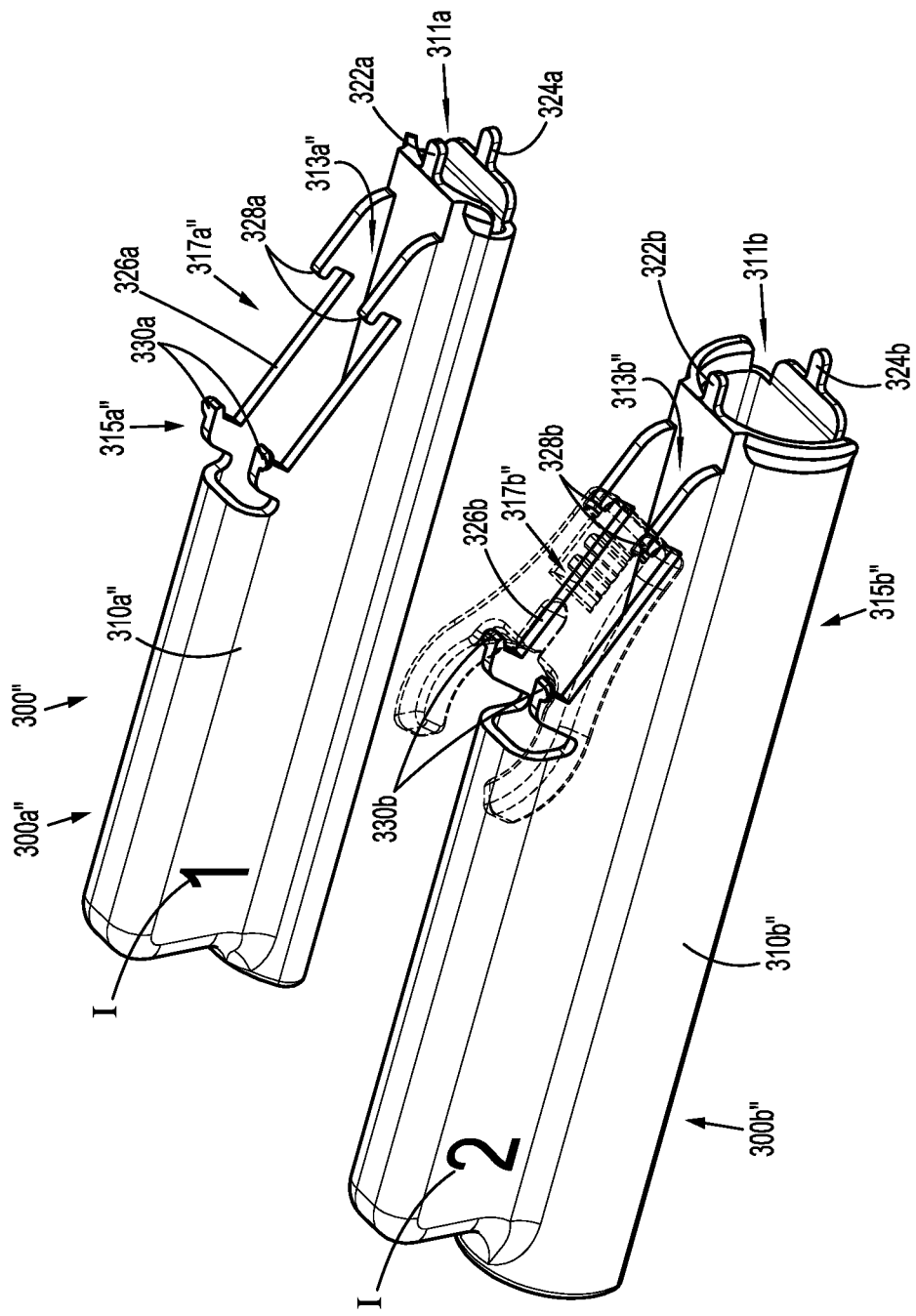
FIG. 14 is a perspective view of a surgical buttress applicator in accordance with yet another embodiment of the present disclosure.
Figure 15:
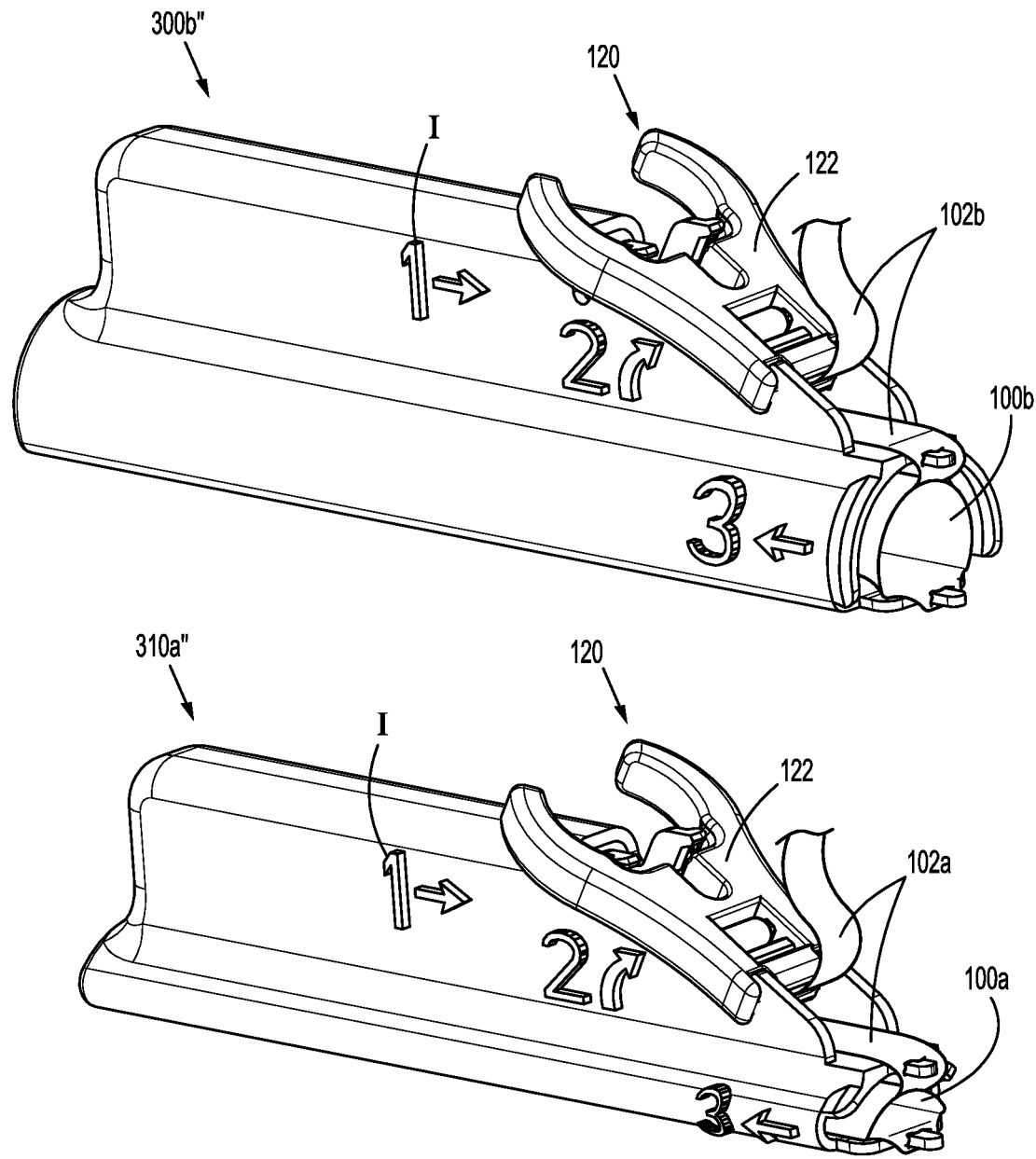
FIG. 15 is a perspective view of the surgical buttress applicator of FIG. 14, loaded with anvil and cartridge buttresses.

As another example, as shown in FIGS. 14 and 15, a surgical buttress applicator 300" includes anvil and cartridge buttress loading units 300*a*", 300*b*" each having a buttress cavity 311*a*, 311*b* including a first tab 322*a*, 322*b* and a second tab 324*a*, 324*b* extending proximally therefrom, and a strap cavity 313*a*", 313*b*". A proximal end portion 315*a*", 315*b*" of the strap cavity 313*a*", 313*b*" includes a cutout 317*a*", 317*b*" defined therein. The cutout 317*a*", 317*b*" has an oblique wall 326*a*, 326*b* slanting towards the buttress cavity 311*a*, 311*b*. The cutout 317*a*", 317*b*" is defined between a proximal pair of hook arms 328*a*, 328*b* and a distal pair of hook arms 330*a*, 330*b* configured to releasably engage the body 122 of the clip 120 such that the body 122 of the clip 120 lies against the oblique wall 326*a*, 326*b* and the clip 120 covers the opening into the strap cavity 313*a*", 313*b*". Indicia "I" is provided on the body 310*a*", 310*b*" of the anvil and cartridge buttress loading units 300*a*", 300*b*" to indicate proper loading onto a surgical stapler.

Figure 16:
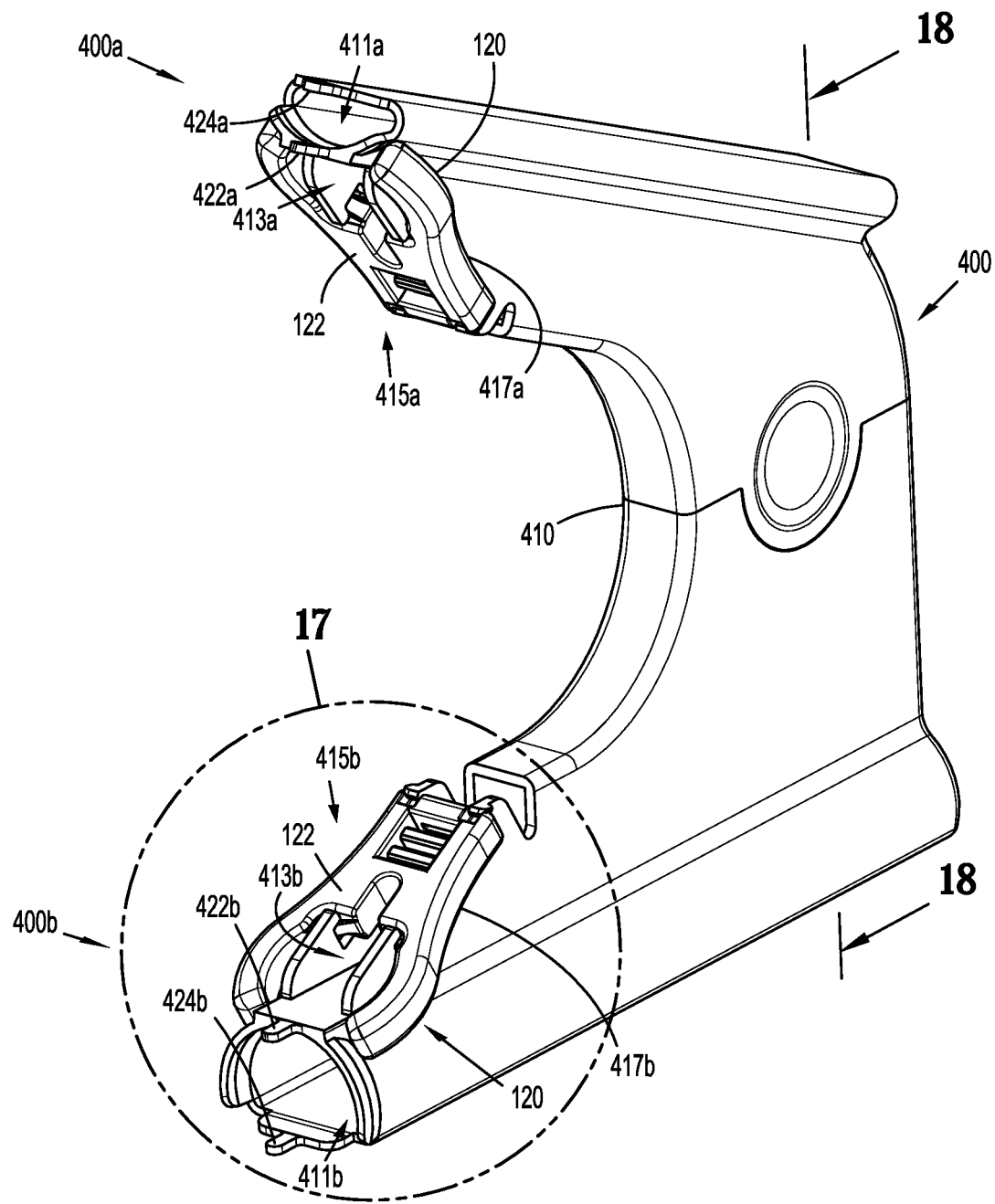
FIG. 16 is a perspective view of a surgical buttress applicator in accordance with another embodiment of the present disclosure.
Figure 17:
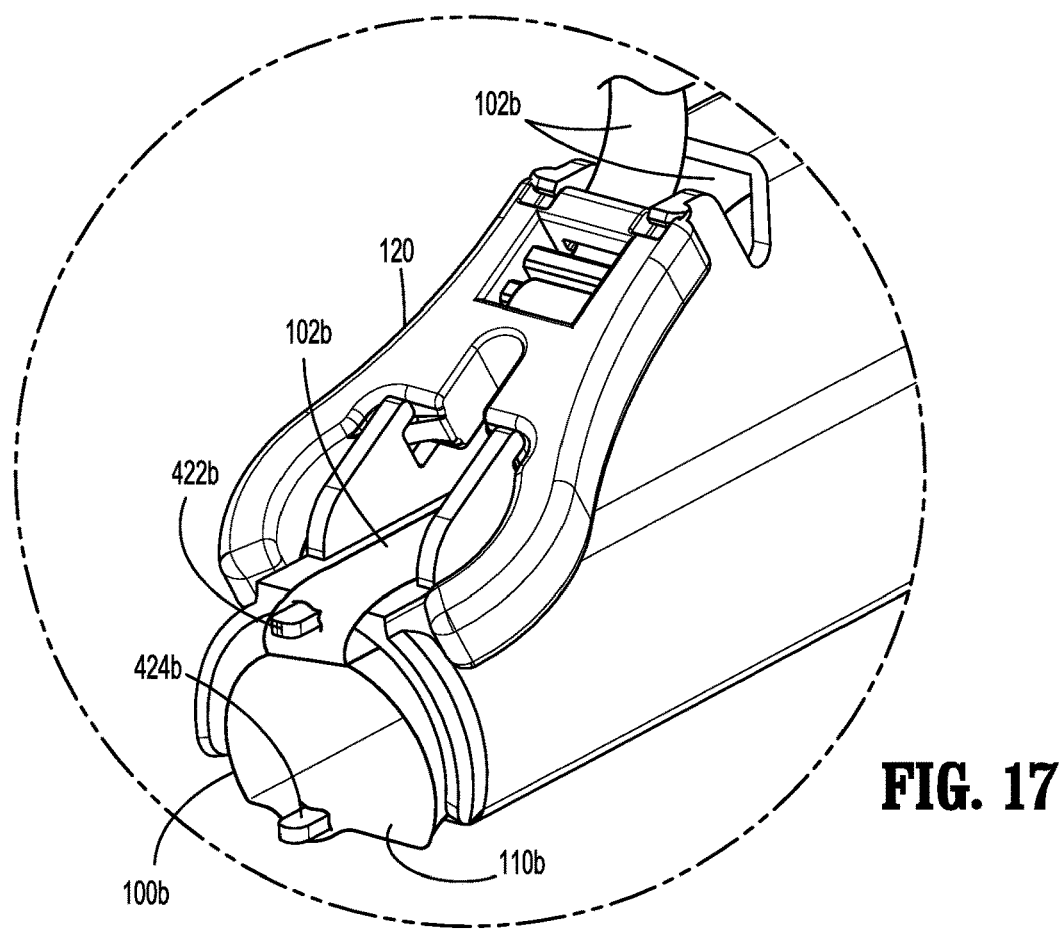
FIG. 17 is an enlarged view of the indicated area of detail of FIG. 16.
Figure 18:
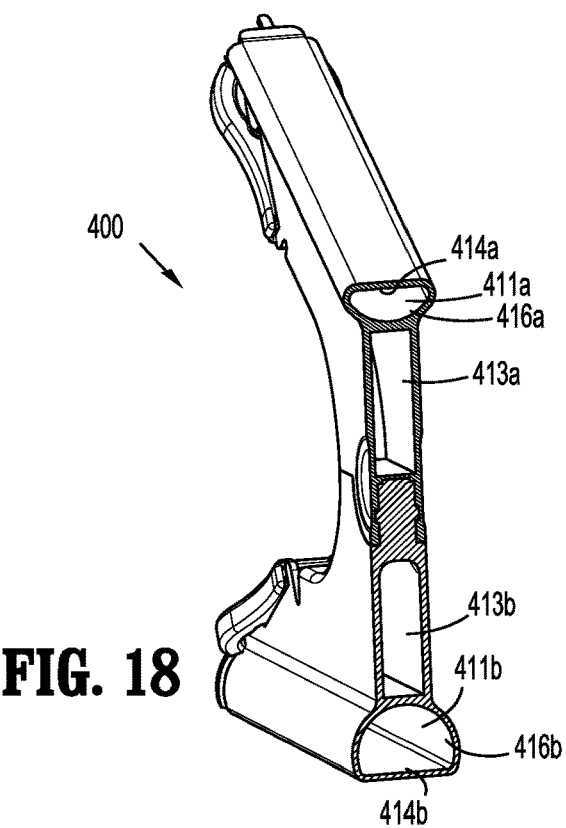
FIG. 18 is a cross-sectional view of the surgical buttress applicator of FIG. 16, taken along section line 18-18 of FIG. 16.

Turning now to FIG. 16, a surgical buttress applicator 400 includes a body 410 having an anvil buttress loading side 400*a* secured to a cartridge buttress loading side 400*b*. As shown in FIGS. 16-18, the anvil buttress loading side 400*a* of the surgical buttress applicator 400 includes a buttress cavity 411*a* and a strap cavity 413*a*, and the cartridge buttress loading side 400*b* includes a buttress cavity 411*b* and a strap cavity 413*b*. The buttress cavities 411*a*, 411*b* are configured to retain the tubular bodies 110*a*, 110*b* of the respective anvil and cartridge buttresses 100*a*, 100*b* therein, and the strap cavities 413*a*, 413*b* are configured to retain the straps 102*a*, 102*b* of the respective anvil and cartridge buttresses 100*a*, 100*b* therein.

The buttress cavities 411*a*, 411*b* each includes a first or substantially flat wall section 414*a*, 414*b* corresponding to the tissue facing surface 48, 56 (FIG. 2) of the anvil or staple cartridge assembly 40, 50, and a second or rounded wall section 416*a*, 416*b* configured to extend around the anvil or staple cartridge assembly 40, 50 and over the outwardly facing surface 46, 53 (FIG. 2) of the anvil or staple cartridge assembly 40, 50. The configuration of the buttress cavities 411*a*, 411*b* allow the tubular bodies 110*a*, 110*b* of the anvil and cartridge buttresses 100*a*, 100*b* to be retained therein in an open configuration for slidably receiving the anvil or staple cartridge assembly 40, 50 therein. First and second tabs 422*a*, 424*b* extend proximally and axially from the respective first and second wall sections 414*a*, 416*a* of the buttress cavity 411*a* of the anvil buttress loading side 400*a* in opposed relation relative to each other, and first and second tabs 422*b*, 424*b* extend proximally and axially from the respective first and second wall sections 414*b*, 416*b* of the buttress cavity 411*b* of the cartridge buttress loading side 400*b* in opposed relation relative to each other. The strap cavities 413*a*, 413*b* each includes a cutout 417*a*, 417*b* defined in the proximal end portion 415*a*, 415*b* of the strap cavity 413*a*, 413*b*, as described above with respect to the cutout 317*a*", 317*b*" of the surgical buttress applicator 300", that is releasably engageable with the body 122 of the clip 120 for retaining the clip 120 thereto. The anvil and cartridge buttress loading sides 400*a*, 400*b* are interconnected by, for example, press fit.

The anvil and cartridge buttresses 100*a*, 100*b* are loaded into the surgical buttress applicator 400 and further, the anvil and cartridge buttresses 100*a*, 100*b* are applied to the surgical stapler 1, in a similar manner as described above with respect to the surgical buttress applicators 200, 300. The surgical buttress applicator 400 may further include indicia to indicate the order of loading (e.g., indicating loading of the anvil assembly 40 before the staple cartridge assembly 50). A loaded surgical stapler 1 is used, for example, as discussed above with regard to surgical buttress applicator 200.

Figure 19:
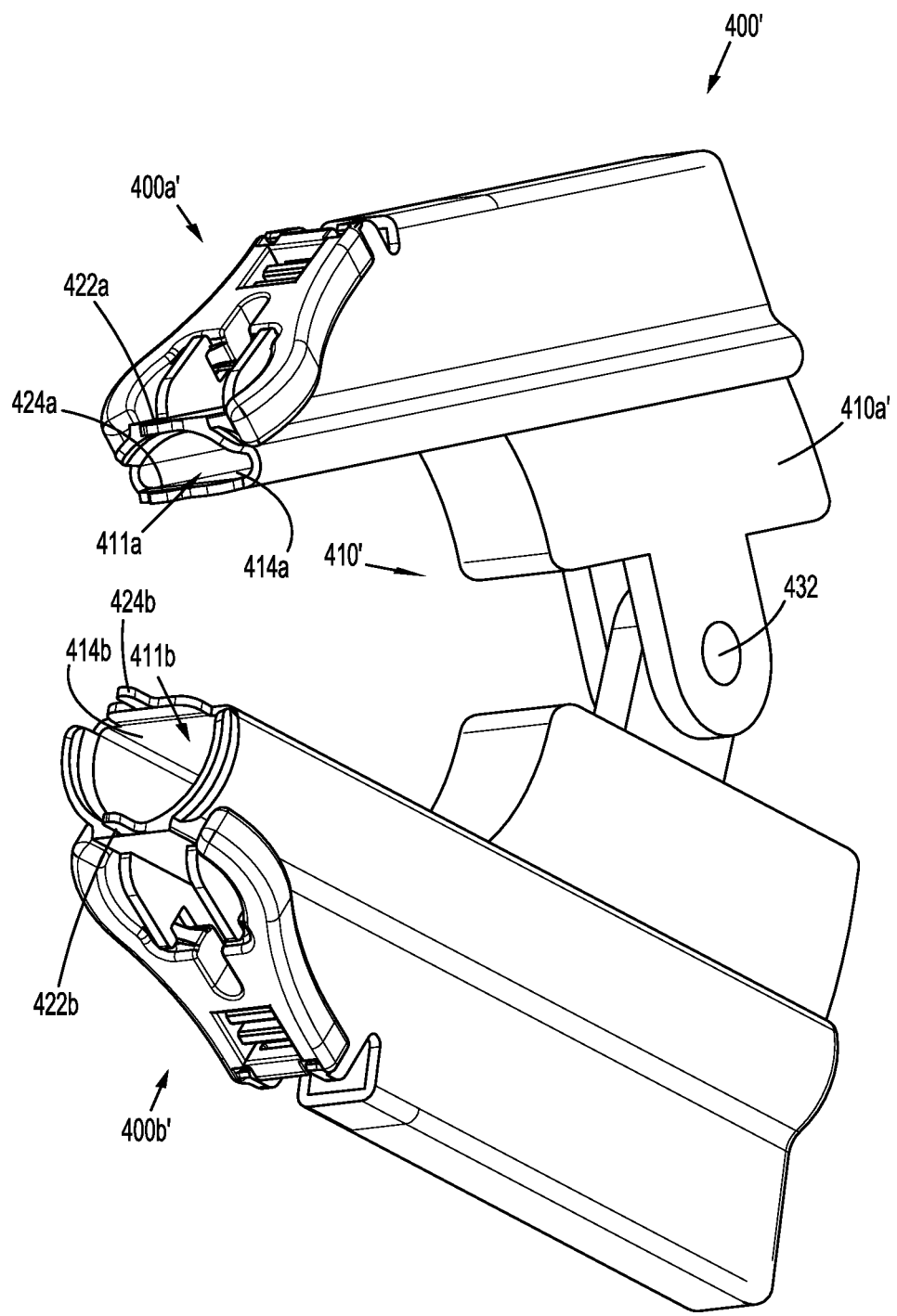
FIG. 19 is a perspective view of a surgical buttress applicator in accordance with another embodiment of the present disclosure.

With reference now to FIG. 19, a surgical buttress applicator 400' is substantially similar to surgical buttress applicator 400, however, the anvil and cartridge buttress loading sides 400*a*', 400*b*' are hingedly connected so that the anvil and staple cartridge assemblies 40, 50 (FIG. 1) can be loaded at the same time. Accordingly, the buttress cavities 411*a*, 411*b* are oriented so that the anvil and staple cartridge assemblies 40, 50 can be inserted therein at the same time (e.g., the first wall sections 414*a*, 414*b* of the buttress cavities 411*a*, 411*b* face each other), and a hinge 432 is disposed about the distal end portion 410a' of the body 410' to allow the anvil and cartridge buttress loading sides 400a', 400b' to be moved between approximated and unapproximated positions (e.g., corresponding to the closed and open positions of the end effector 30) to allow for the surgical stapler 1 to be manipulated thereon.

Figure 20:
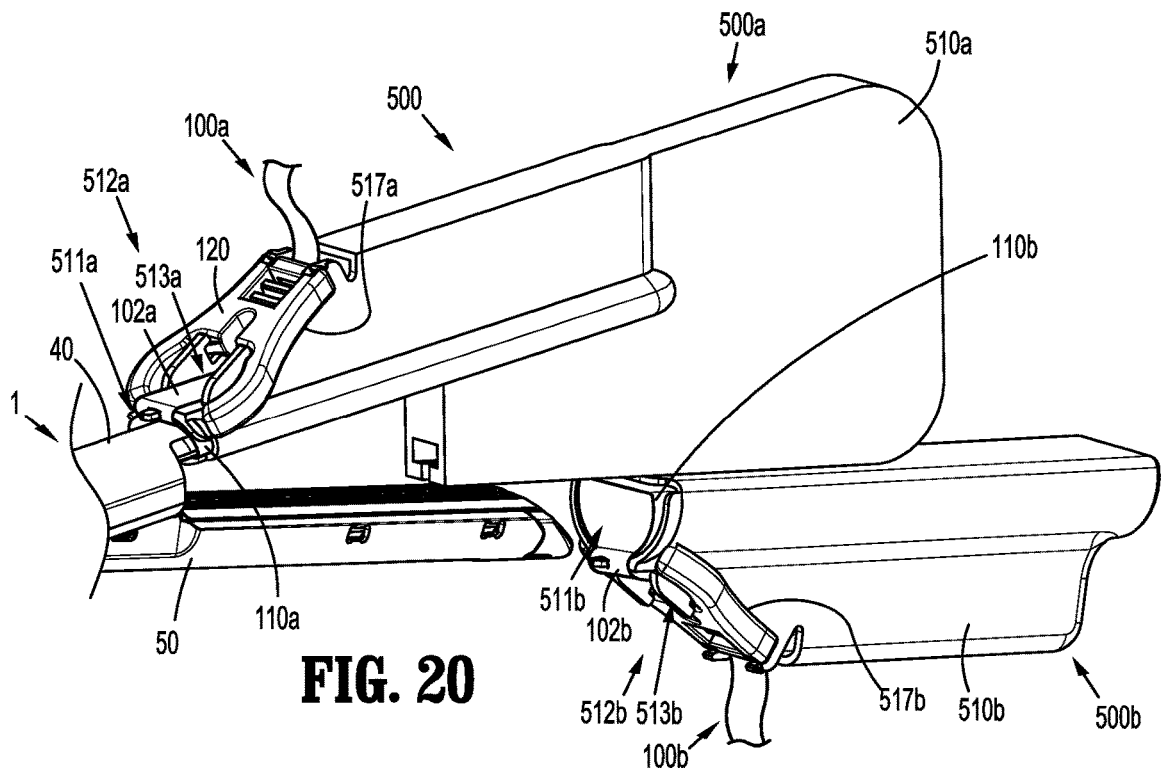
FIG. 20 is a perspective view of a surgical buttress applicator in accordance with yet another embodiment of the present disclosure, shown in an initial position.

FIG. 20 illustrates a surgical buttress applicator 500 in accordance with another embodiment of the present disclosure. The surgical buttress applicator 500 includes an anvil buttress loading unit 500a slidable relative to a cartridge buttress loading unit 500b. The anvil and cartridge buttress loading units 500a, 500b each includes a body 510a, 510b defining a buttress cavity 511a, 511b and a strap cavity 513a, 513b therein. The buttress cavity 511a, 511b is sized and shaped to retain the tubular body 110a, 110b of the anvil or cartridge buttress 100a, 100b therein in an open configuration, and to further slidably receive the respective anvil or staple cartridge assembly 40, 50 of the surgical stapler 1 therein. The strap cavities 513a, 513b are configured to retain the straps 102a, 102b of the respective anvil and cartridge buttresses 100a, 100b therein and to releasably engage the clips 120. The configuration of the buttress cavities 511a, 511b and the strap cavities 513a, 513b is substantially similar to those of the surgical buttress applicator 400.

Figure 21:
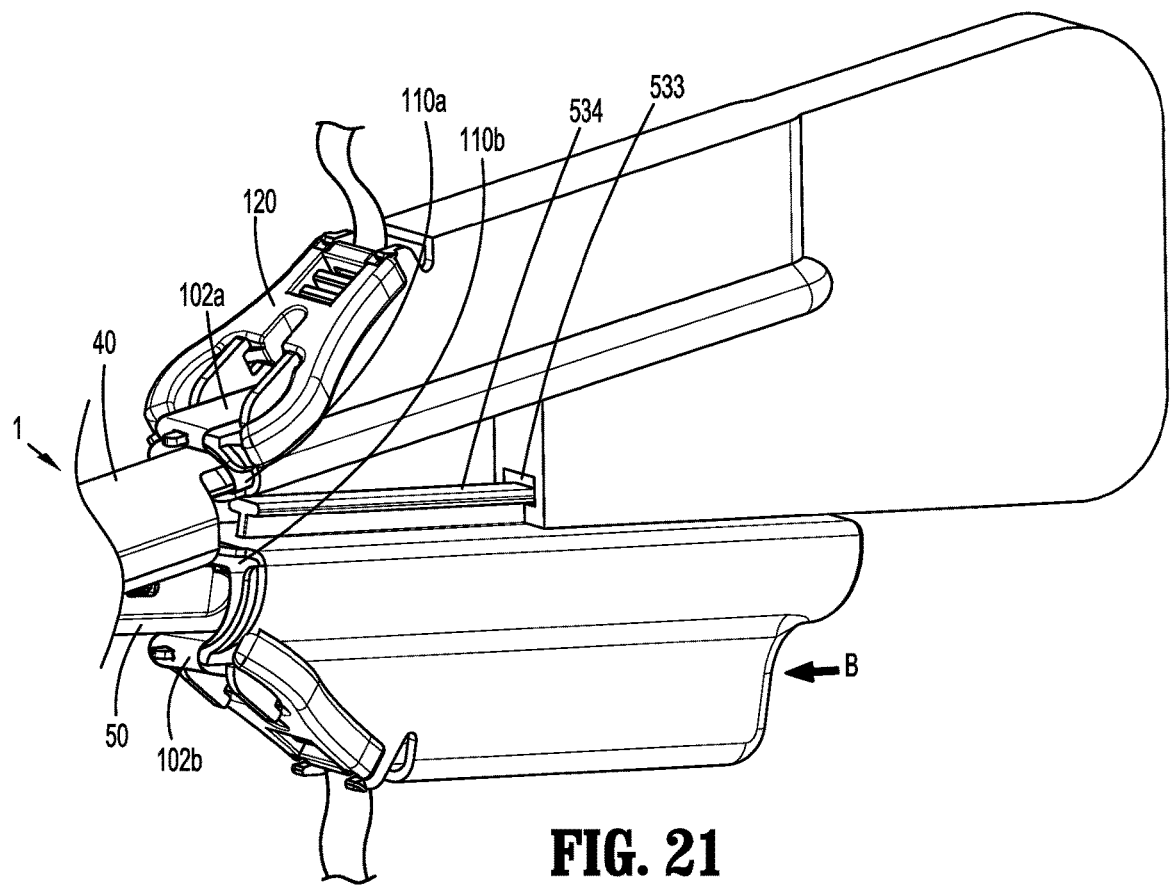
FIG. 21 is a perspective view of the surgical buttress applicator of FIG. 20, shown in an actuated position.

As shown in FIGS. 20 and 21, opposed walls of the anvil and cartridge buttress loading units 500a, 500b include a complementary groove 533 and rail 534 so that the anvil and buttress loading units 500a, 500b are longitudinally slidable relative to each other. While the anvil buttress loading unit 500a is shown including the groove 533 and the cartridge buttress loading unit 500b is shown including the rail 534, it should be understood that the groove 533 and rail 534 placement may be reversed or other complementary structures for facilitating sliding movement between the anvil and cartridge buttress loading units 500a, 500b may be utilized as is within the purview of those skilled in the art.

As shown in FIG. 20, the surgical buttress applicator 500 is biased in a first or initial position in which the anvil buttress loading unit 500a is disposed proximally of the cartridge buttress loading unit 500b (e.g., longitudinally offset). Upon loading, the anvil assembly 40 of the surgical stapler 1 is aligned and inserted into the buttress cavity 511a of the anvil buttress loading unit 500a. The cartridge buttress loading unit 500b is then slid proximally towards the anvil buttress loading unit 500a in the direction of arrow "B," as shown in FIG. 21, such that the staple cartridge assembly 50 of the surgical stapler 1 enters the buttress cavity 511b of the cartridge buttress loading unit 500b. In the second or actuated position, the anvil and cartridge buttress loading units 500a, 500b are longitudinally aligned. With the surgical buttress applicator 500 applied to the anvil and staple cartridge assemblies 40, 50 of the surgical stapler 1, the clips 120 are detached from the respective anvil and cartridge buttress loading units 500a, 500b and pulled proximally towards the user thereby unfurling the straps 102a, 102b from the strap cavities 513a, 513b of the anvil and cartridge buttress loading units 500a, 500b. The clips 120 are then secured to the elongate tubular body portion 20 of the surgical stapler 1 and the surgical buttress applicator 500 is pulled distally from the surgical stapler 1 such that the anvil and cartridge buttresses 100a, 100b are released from the bodies 510a, 510b of the anvil and cartridge buttress loading units 500a, 500b and retained on the respective anvil and staple cartridge assemblies 40, 50 of the surgical stapler 1. The loaded surgical stapler 1 is now ready for use.

FIG. 22 shows a surgical buttress applicator 600 including an anvil buttress loading unit 600a hingedly connected to a cartridge buttress loading unit 600b. The anvil and cartridge buttress loading units 600a, 600b each includes a body 610a, 610b defining a buttress cavity 611a, 611b and a strap cavity 613a, 613b therein. The buttress cavity 611a, 611b is sized and shaped to retain the tubular body 110a, 110b of the anvil or cartridge buttress 100a, 100b therein in an open configuration, and to further slidably receive the respective anvil or cartridge assembly 40, 50 (FIG. 1) of the surgical stapler 1 therein. The strap cavities 613a, 613b are configured to retain the straps 102a, 102b of the respective anvil and cartridge buttresses 100a, 100b therein and to releasably engage the clips 120. The configuration of the buttress cavities 611a, 611b and the strap cavities 613a, 613b is substantially similar to those of the surgical buttress applicator 300.

The anvil and cartridge buttress loading units 600a, 600b are movable relative to each other about a hinge 632. The hinge 632 includes a hinge post 632a extending laterally from a distal end 612a of the anvil buttress loading unit 600a, and a pin 632b extending laterally from a proximal end 612b of the cartridge buttress loading unit 600b and into the hinge post 632a for pivotal movement about an axis "Y" transverse to a longitudinal axis "X."

In a first or initial position, shown in FIG. 22, the anvil and cartridge buttress loading units 600a, 600b are longitudinally aligned along the longitudinal axis "X" such that the cartridge buttress loading unit 600b is blocked (e.g., the openings into the buttress and strap cavities 611a, 613a) by the anvil buttress loading unit 600a, and only the anvil buttress loading unit 600a is accessible. After loading the anvil assembly 40 with the anvil buttress 100a disposed within the anvil buttress loading unit 600a, the anvil buttress loading unit 600a is moved laterally relative to the cartridge buttress loading unit 600b by rotating the anvil buttress loading unit 600a about the hinge 632 in the direction of arrow "C," as shown in FIG. 23, to a second or actuated position to unblock the cartridge buttress loading unit 600b for loading onto the staple cartridge assembly 50 of the surgical stapler 1.

Figure 24:
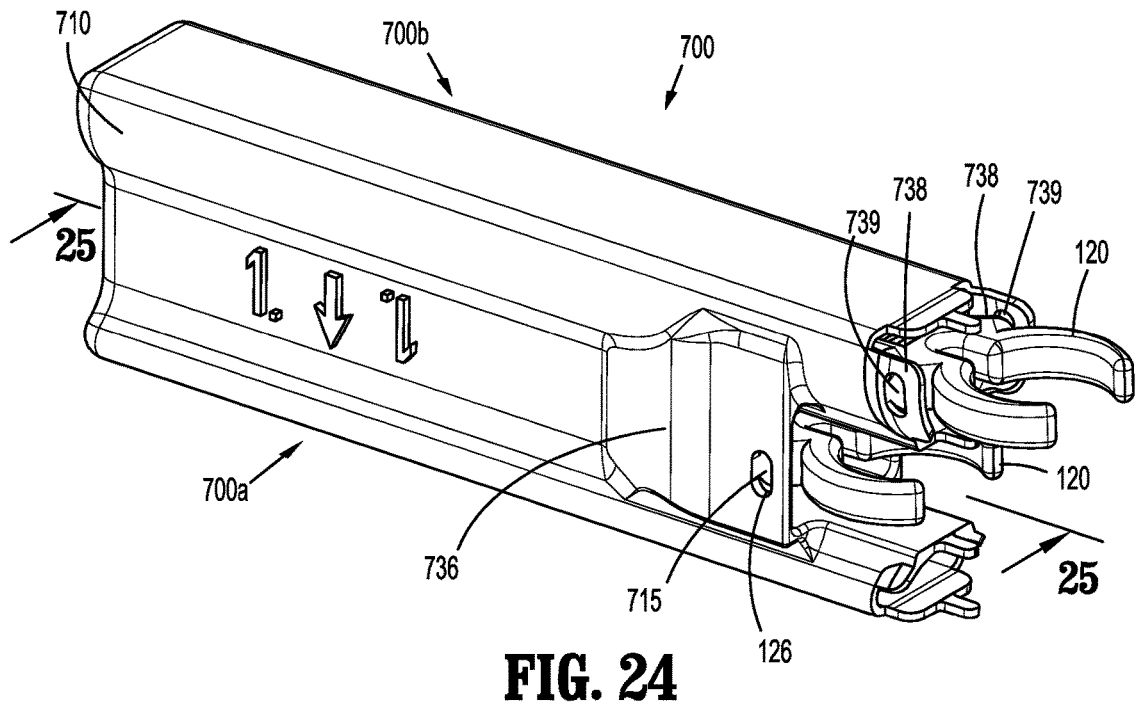
FIG. 24 is a perspective view of a surgical buttress applicator in accordance with another embodiment of the present disclosure.

FIG. 24 shows a surgical buttress applicator 700 including a body 710 having an anvil buttress loading unit 700a and a cartridge buttress loading unit 700b. As shown in FIGS. 24-25B, the anvil and cartridge buttress loading units 700a, 700b each defines a buttress cavity 711a, 711b and together, define a single strap cavity 713 in the surgical buttress applicator 700. The buttress cavity 711a, 711b is sized and shaped to retain the tubular body 110a, 110b of the anvil or cartridge buttress 100a, 100b therein in an open configuration, and to further slidably receive the respective anvil or cartridge assembly 40, 50 (FIG. 1) of the surgical stapler 1 therein. The configuration of the buttress cavities 711a, 711b is substantially similar to those described above with respect to, for example, surgical buttress applicator 200, 300.

The strap cavity 713 is configured to retain the straps 102a, 102b of the respective anvil and cartridge buttresses 100a, 100b therein. The strap cavity 713 includes a pair of flexible arms 736 disposed in opposed relation relative to each other and configured to releasably engage a clip 120. An opening 715 may be defined in one or both arms of the pair of flexible arms 736 for engaging the boss 126 of the clip 120. Similarly, the buttress cavity 711b of the cartridge buttress loading unit 700b includes a pair of flexible arms 738 disposed in opposed relation relative to each other and configured to releasably engage a clip 120. An opening 739 may be defined in one or both arms of the pair of flexible arms 738 for engaging the boss 126 of the clip 120.

Figure 25A:
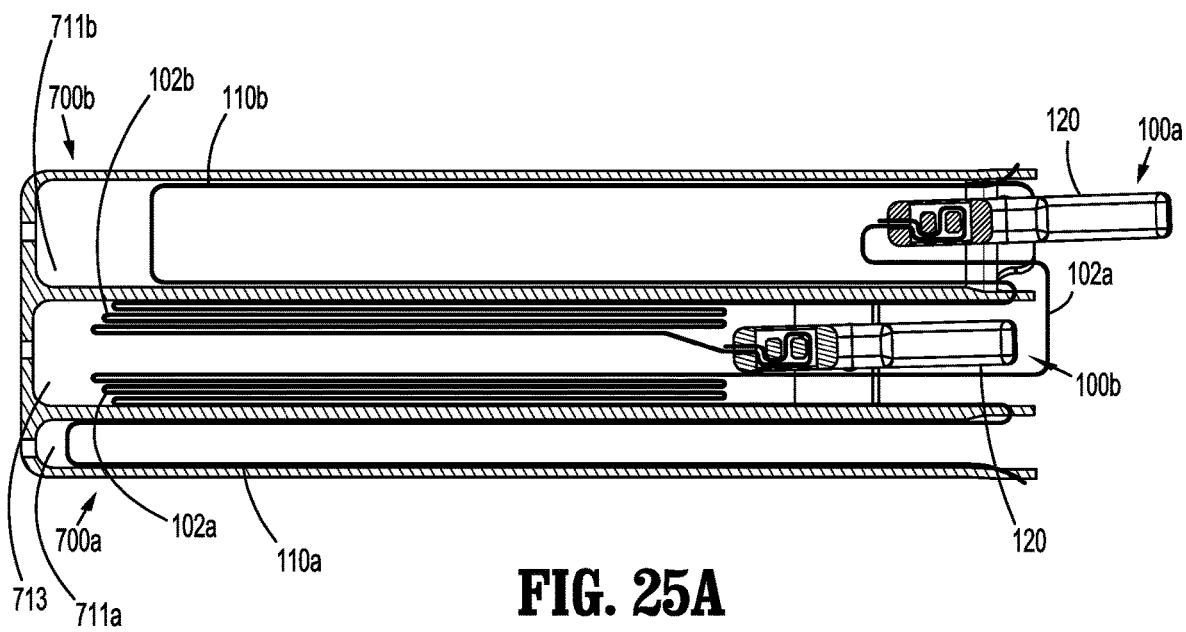
FIGS. 25A and 25B are cross-sectional views of embodiments of the surgical buttress applicator of FIG. 24, taken along section line 25-25 of FIG. 24.
Figure 25B:
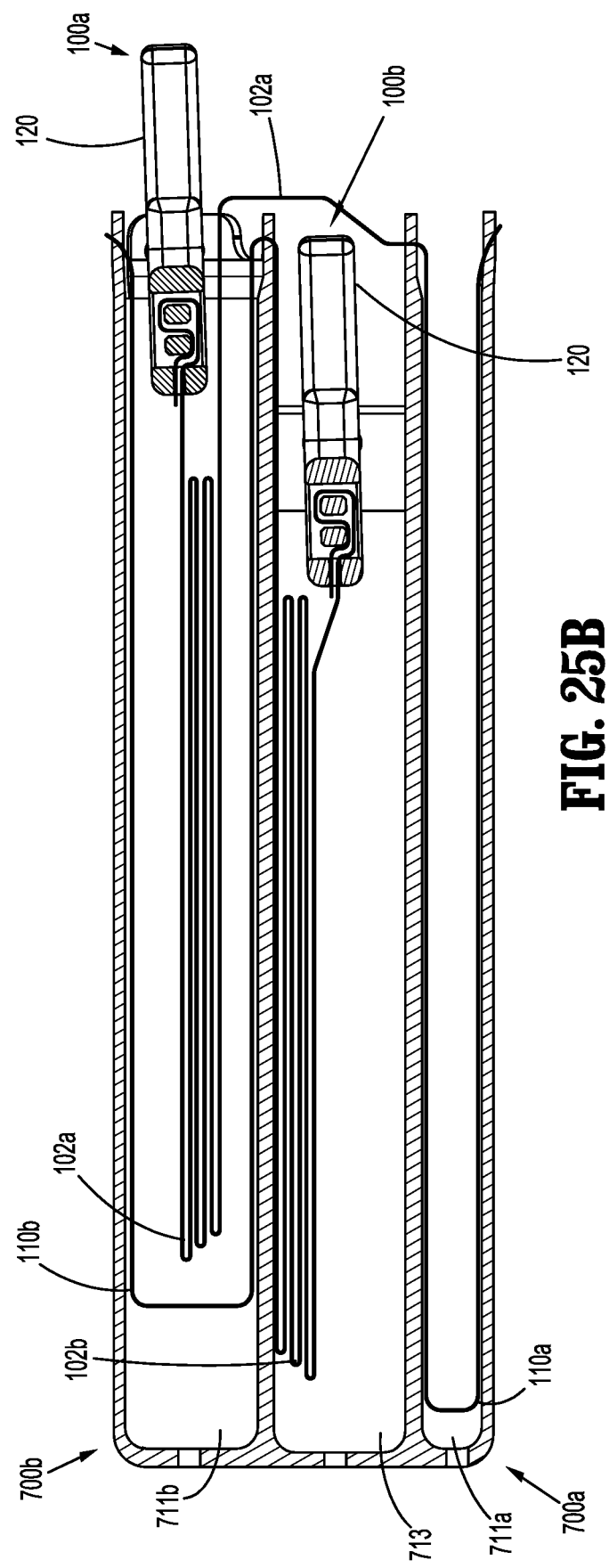

In a loaded configuration, as shown in FIG. 25A, the tubular body 110b of the cartridge buttress 100b is positioned within the buttress cavity 711b of the cartridge buttress loading unit 700b, the strap 102b of the cartridge buttress 100b is passed into the strap cavity 713, and the clip 120 of the cartridge buttress 100b is engaged with the flexible arms 736 of the strap cavity 713. The tubular body 110a of the anvil buttress 100a is positioned within the buttress cavity 711a of the anvil buttress loading unit 700a, a majority of the strap 102a of the anvil buttress 100a is passed into the strap cavity 713, and the clip 120 of the anvil buttress 100a is engaged with the flexible arms 738 of the buttress cavity 711b of the cartridge buttress loading unit 700b such that the clip 120 of the anvil buttress 100a blocks the buttress cavity 711b of the cartridge buttress loading unit 700b and the anvil buttress loading unit 700a has to be loaded first before the cartridge buttress loading unit 700b can be accessed by a user. Alternatively, as shown in FIG. 25B, the strap 102a of the anvil buttress 100a may bypass the strap cavity 713 and be positioned within the tubular body 710b of the cartridge buttress 100b. The anvil and cartridge buttresses 100a, 100b are applied to the surgical stapler 1, in a similar manner as described above with respect to the surgical buttress applicator 200.

Figure 26:
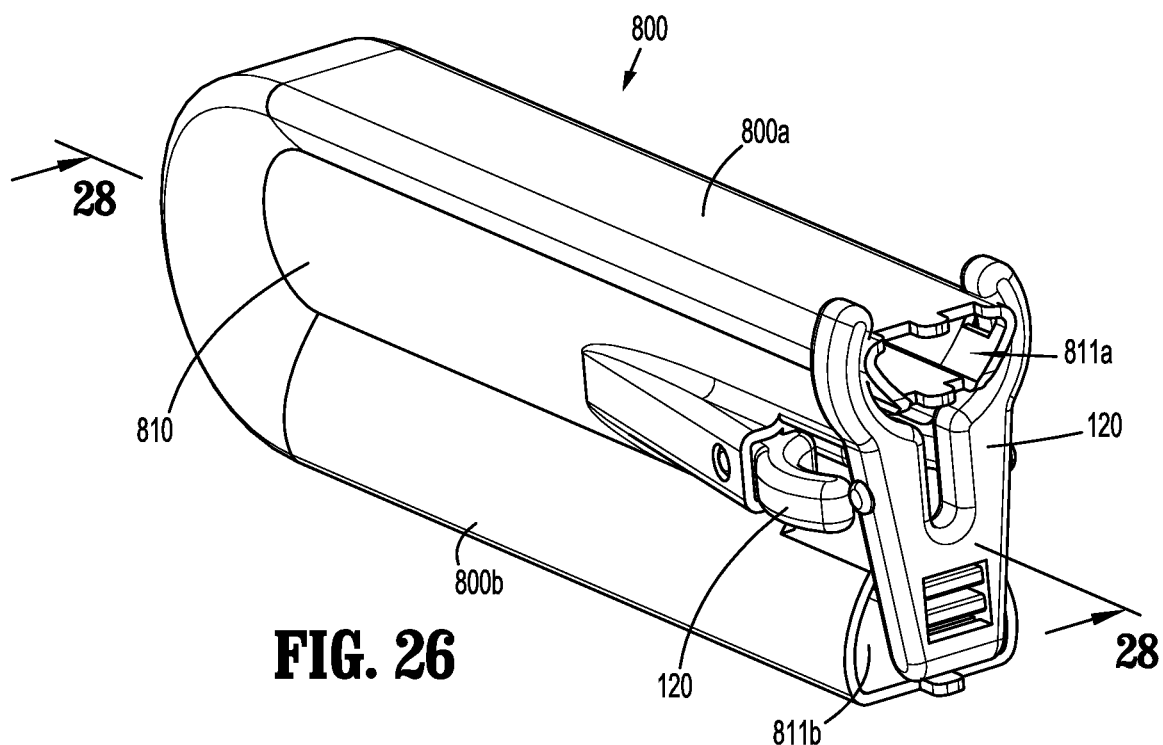
FIGS. 26 and 27 are perspective views of a surgical buttress applicator in accordance with yet another embodiment of the present disclosure.
Figure 27:
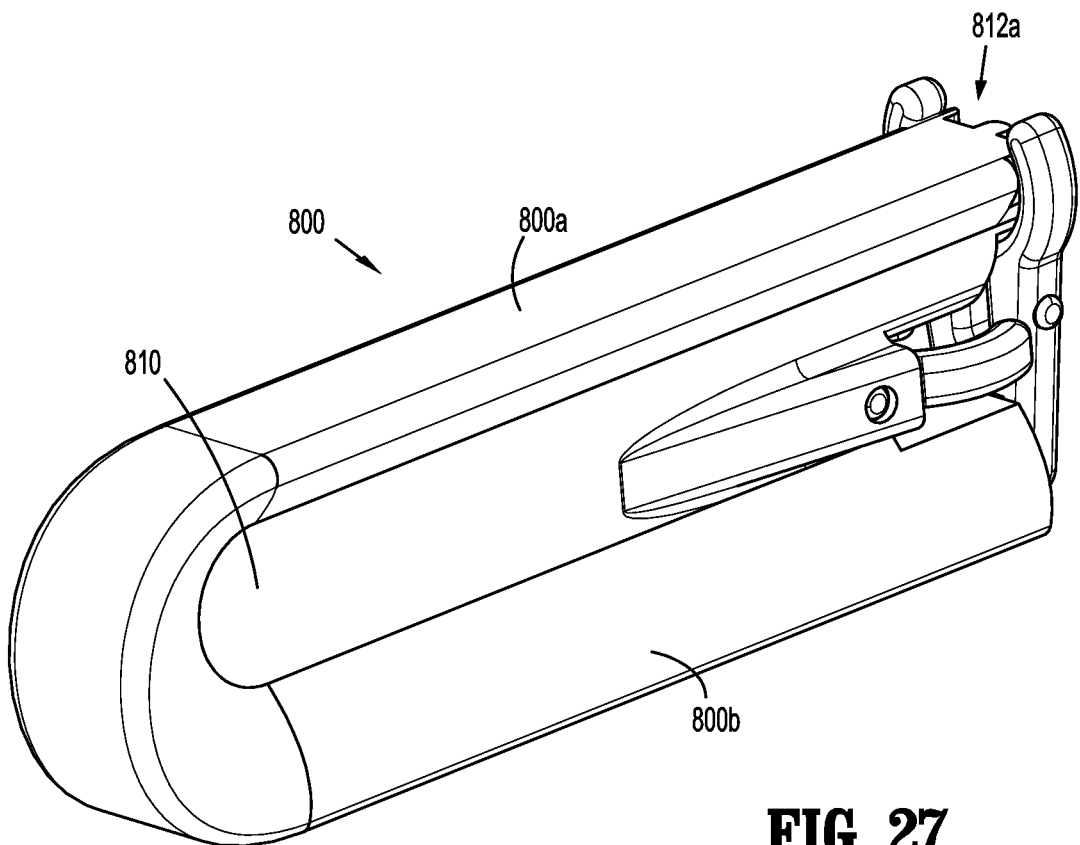
Figure 28A:
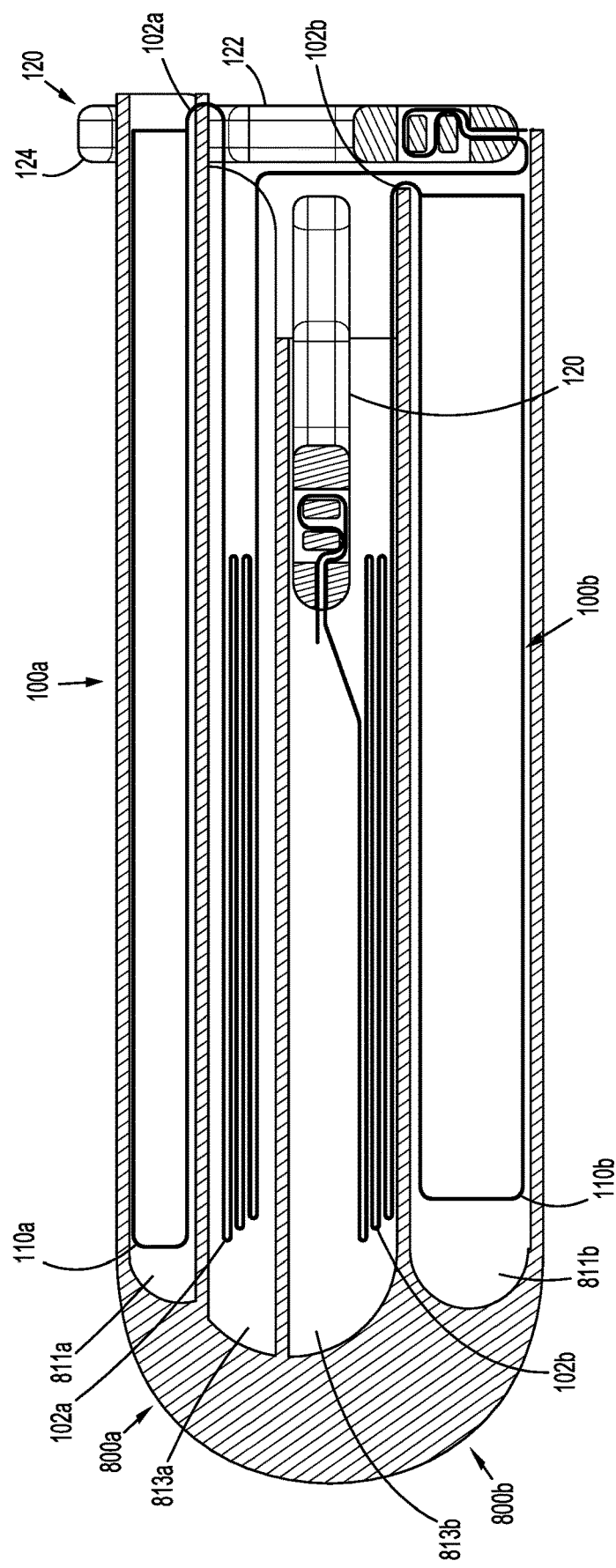
FIGS. 28A and 28B are cross-sectional views of embodiments of the surgical buttress applicator of FIGS. 26 and 27, taken along section line 28-28 of FIG. 26.
Figure 28B:
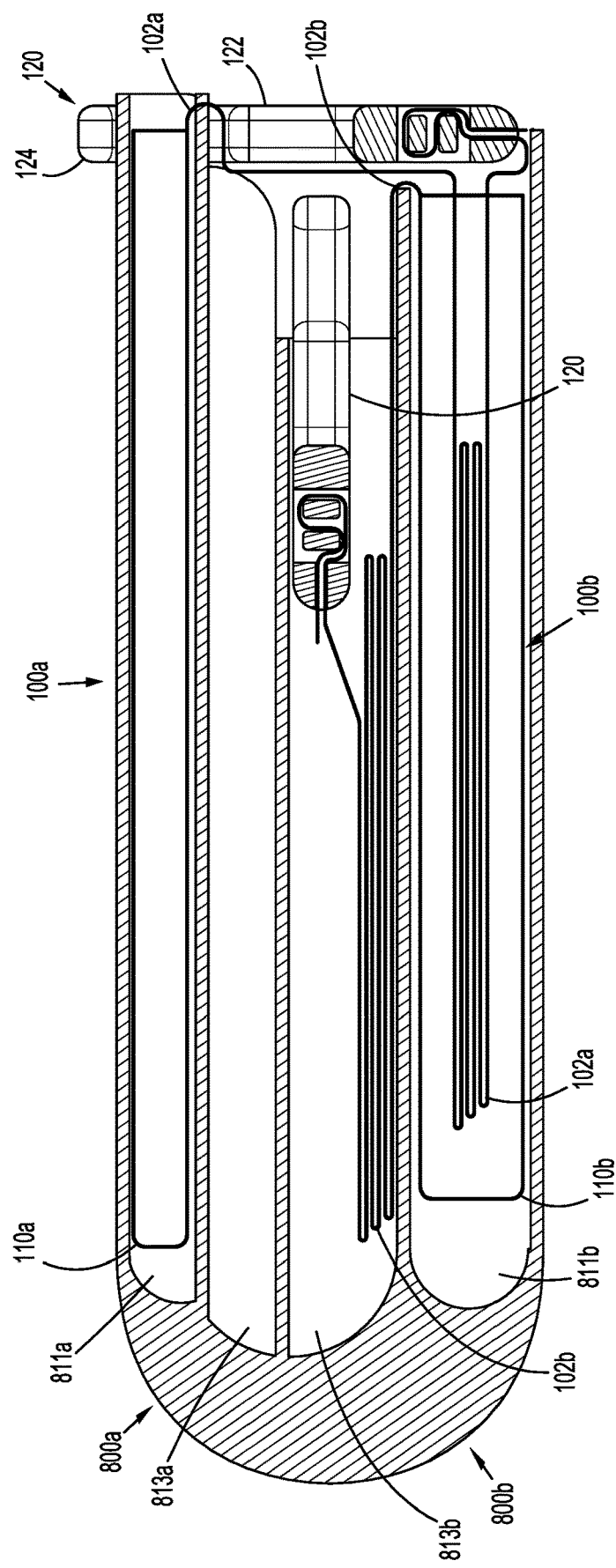

FIGS. 26 and 27 show a surgical buttress applicator 800 including a body 810 having an anvil buttress loading unit 800a and a cartridge buttress loading unit 800b. The anvil and cartridge buttress loading units 800a, 800b each defines a buttress cavity 811a, 811b and a strap cavity 813a, 813b as shown in FIG. 28A, or a single strap cavity 813, as shown in FIG. 28B. The buttress cavity 811a, 811b is sized and shaped to retain the tubular body 110a, 110b of the anvil or cartridge buttress 100a, 100b therein in an open configuration, and to further slidably receive the respective anvil or cartridge assembly 40, 50 (FIG. 1) of the surgical stapler 1 therein. The configuration of the buttress cavities 811a, 811b is substantially similar to those described above with respect to, for example, surgical buttress applicator 200, 300.

The strap cavities 813a, 813b are configured to retain the straps 102a, 102b of the respective anvil and cartridge buttresses 100a, 100b therein. The strap cavity 813b of the cartridge buttress loading unit 800b is configured to releasably engage a clip 120 as discussed above with regard to surgical buttress applicators 300, 300', 300".

In a loaded configuration, as shown in FIG. 28A, the tubular body 110b of the cartridge buttress 100b is positioned within the buttress cavity 811b of the cartridge buttress loading unit 800b, the strap 102b of the cartridge buttress 100b is passed into the strap cavity 813b of the cartridge buttress loading unit 800b, and the clip 120 of the cartridge buttress 100b is engaged with the strap cavity 813b. The tubular body 110a of the anvil buttress 100a is positioned within the buttress cavity 811a of the anvil buttress loading unit 800a, a majority of the strap 102a of the anvil buttress 100a is passed into the strap cavity 813a of the anvil buttress loading unit 800a, and the pair of fingers 124 of the clip 120 of the anvil buttress 100a is engaged with a proximal end portion 812a surrounding the buttress cavity 811a of the anvil buttress loading unit 800a such that the body 122 of the clip 120 blocks the buttress cavity 811b of the cartridge buttress loading unit 800b and the anvil buttress loading unit 800a has to be loaded first before the cartridge buttress loading unit 800b can be accessed by a user. Alternatively, as shown in FIG. 28B, the strap 102a of the anvil buttress 100a may be positioned within the tubular body 110b of the cartridge buttress 100b. The anvil and cartridge buttresses 100a, 100b are applied to the surgical stapler 1, in a similar manner as described above with respect to the surgical buttress applicator 200.

Figure 30:
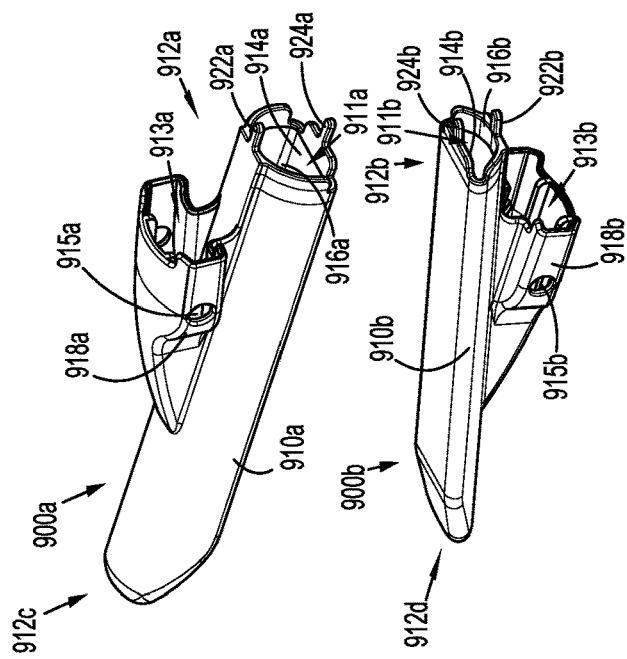
FIG. 30 is a perspective view of anvil and cartridge buttress loading units of the surgical buttress applicator of FIG. 29.
Figure 29:
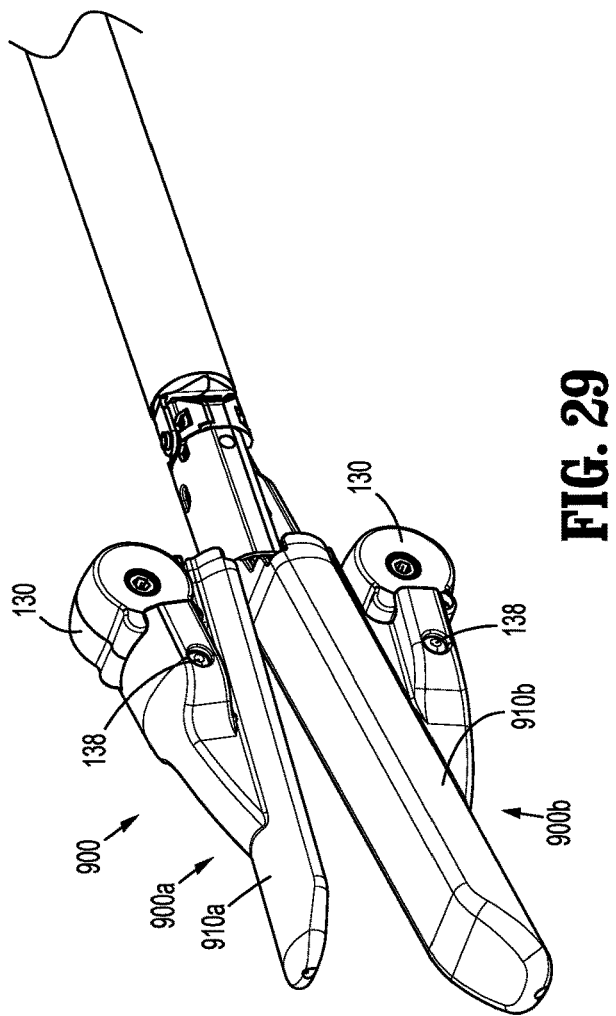
FIG. 29 is a perspective view of a surgical buttress applicator in accordance with another embodiment of the present disclosure, shown loaded on the surgical stapling apparatus of FIG. 1.

Turning now to FIGS. 29 and 30, a surgical buttress applicator 900 includes an anvil buttress loading unit 900a and a cartridge buttress loading unit 900b. The anvil and cartridge buttress loading units 900a, 900b each includes a body 910a, 910b having a proximal end 912a, 912b and a distal end 912c, 912d, and each defines a buttress cavity 911a, 911b and a clip cavity 913a, 913b therein. The buttress cavity 911a, 911b is sized and shaped to retain the tubular body 110a, 110b (FIG. 33) of the anvil or cartridge buttress 100a, 100b therein in an open configuration, and to further, slidably receive the respective anvil or staple cartridge assembly 40, 50 of the surgical stapler 1 therein. The buttress cavities 911a, 911b each includes a first or substantially flat wall section 914a, 914b corresponding to the tissue facing surface 48, 56 (FIG. 2) of the anvil or staple cartridge assembly 40, 50, and a second or rounded wall section 916a, 916b configured to extend around the anvil or staple cartridge assembly 40, 50 and over the outwardly facing surface 46, 53 (FIG. 2) of the anvil or staple cartridge assembly 40, 50.

The proximal end 912a of the anvil buttress loading unit 900a further includes first and second tabs 922a, 924a extending proximally and axially from the respective first and second wall sections 914a, 916a of the buttress cavity 911a in opposed relation relative to each other. The first and second tabs 922a, 924a are configured to engage the anvil buttress 100a and aid in retaining the tubular body 110a in an open configuration within the buttress cavity 911a. Likewise, the proximal end 912b of the cartridge buttress loading unit 900b includes first and second tabs 922b, 924b extending proximally and axially from the respective first and second wall sections 914b, 916b of the buttress cavity 911b in opposed relation relative to each other, and are configured to engage the cartridge buttress 100b and aid in retaining the tubular body 110b in an open configuration within the buttress cavity 911b.

The clip cavity 913a, 913b is configured to retain at least a portion of a clip 130 that is secured to the respective anvil and cartridge buttress 100a, 100b therein. As shown in FIGS. 31-33, the clip 130 includes a body 132 having a first end portion 132a including at least one opening or slot 133 through which the strap 102a, 102b of the anvil or cartridge buttress 100a, 100b is threaded through. The slot 133 extends into a strap cavity 135 defined within the body 132. The strap cavity 135 includes a reel 136 about which the strap 102a, 102b of the anvil or cartridge buttress 100a, 100b is wound. The reel 136 may be a shaft or a spool rotationally supporting the strap 102a, 102b within the strap cavity 135 of the body 132. The reel 136 is rotatable relative to the body 132 such that the strap 102a, 102b can move from the initial configuration shown in FIG. 31, in which the strap 102a, 102b is wound around the reel 136 and disposed within the strap cavity 135 of the clip 130, to the unfurled configuration shown in FIG. 33, in which the strap 102a, 102b is unwound from the reel 136 and moved outwardly of the strap cavity 135 through the slot 133 defined in the body 132 of the clip 130. A free end 105 of the strap 102a, 102b may be secured to the reel 136 to retain the strap 102a, 102b to the clip 130.

The body 132 has a second end portion 132b including a pair of fingers 134 extending therefrom in opposed relation relative to each other. The pair of fingers 134 are substantially c-shaped or u-shaped and are configured to engage the elongate tubular body portion 20 of the surgical stapler 1 to securely, yet releasably fasten the clip 130 and thus, the strap 102a, 102b of the anvil or cartridge buttress 100a, 100b to the surgical stapler 1.

The clip 130 may include a boss 138 extending from the body 132 (e.g., the fingers 134 of the clip 130) for releasably engaging the body 910a, 910b of the anvil or cartridge buttress loading unit 900a, 900b. As seen in FIGS. 29 and 30, the clip cavities 913a, 913b of the anvil and cartridge buttress loading units 900a, 900b each include an opening 915a, 915b defined in a lateral side or side wall 918a, 918b of the body 910a, 910b of the anvil and cartridge buttress loading units 900a, 900b that is releasably engageable with the boss 138 of the clip 130 for retaining the clip 130 thereto.

To load the surgical buttress applicator 900, the tubular bodies 110a, 110b of the anvil and cartridge buttresses 100a, 100b are positioned in the respective buttress cavity 911a, 911b of the anvil and cartridge buttress loading units 900a, 900b such that the tubular bodies 110a, 110b are open to receive the anvil and staple cartridge assemblies 40, 50 of the surgical stapler 1 therein. The straps 102a, 102b extend out of the buttress cavities 911a, 911b (through the opening in the proximal end 912a, 912b of the body 910a, 910b) and into the strap cavity 135 of the clip 130. The straps 102a, 102b are wound within the strap cavity 135 of the clip 130, and the clip 130 is partially retained within the clip cavity 913a, 913b of the anvil or cartridge buttress loading unit 900a, 900b by positioning the second end portion 132b of the clip 130 within the clip cavity 913a, 913b and engaging the boss 138 of the clip 130 with the opening 915a, 915b defined through the body 910a, 910b of the anvil or cartridge buttress loading unit 900a, 900b.

Further, the anvil and cartridge buttresses 100a, 100b are engaged with the first tabs 922a, 922b and the second tabs 924a, 924b of the respective buttress cavities 911a, 911b of the anvil and buttress loading units 900a, 900b. Specifically, the portion of the strap 102a, 102b extending from the tubular body 110a, 110b and out of the buttress cavity 911a, 911b is secured to the first tab 922a, 922b of the anvil or cartridge buttress loading unit 900a, 900b to help retain the tubular body 110a, 110b within the body 910a, 910b in the open configuration. The first tab 922a, 922b may be positioned through an aperture (not explicitly shown) defined through the strap 102a, 102b. The aperture may be preformed in the anvil or cartridge buttress 100a, 100b, or the aperture may be formed during assembly of the anvil or cartridge buttress 100a, 100b into the surgical buttress applicator 900. The second tab 924a, 924b of the body 910a, 910b of the anvil and cartridge buttress loading units 900a, 900b may be engaged with an aperture (not explicitly shown) defined in the buttress portion 106a, 106b of the anvil and cartridge buttress 100a, 100b to further help retain the tubular body 110a, 110b of the anvil and cartridge buttress 100a, 100b within the body 910a, 910b of the anvil or cartridge buttress loading unit 900a, 900b in the open configuration for receiving the anvil and staple cartridge assembly 40, 50 of the surgical stapler 1 therein.

To load the anvil and cartridge buttresses 100a, 100b onto the surgical stapler 1, the anvil buttress loading unit 900a of the surgical buttress applicator 900 is first applied to the anvil assembly 40 of the surgical stapler 1. A user grasps the body 910a of the anvil buttress loading unit 900a and manipulates the body 910a onto the anvil assembly 40 by aligning the buttress cavity 911a of the anvil buttress loading unit 900a with the distal end of the anvil assembly 40 and sliding the anvil assembly 40 therein until the anvil assembly 40 is positioned within the buttress cavity 911a and/or forward motion of the anvil assembly 40 relative to the anvil buttress loading unit 900a is prohibited.

With the anvil buttress loading unit 900a applied onto the anvil assembly 40 such that the anvil assembly 40 is received within the tubular body 110a of the anvil buttress 100a, as seen in FIG. 29, the clip 130 of the anvil buttress 100a is detached from the body 910a of the anvil buttress loading unit 900a and pulled proximally towards the user thereby unfurling the strap 102a from the strap cavity 135 of the clip 130. The clip 130 is then secured to the elongate tubular body portion 20 of the surgical stapler 1 by engaging the pair of fingers 134 with the elongate tubular body portion 20 at a position proximal of the end effector 30, such as adjacent to the handle assembly 10 of the surgical stapler 1 and/or at least at a location outside of a patient's body during a surgical procedure. The user can then grasp the body 910a of the anvil buttress loading unit 900a and slide it distally off of the anvil assembly 40. The anvil buttress loading unit 900a may be removed from the anvil assembly 40 either prior to, or after, attaching the clip 130 to the surgical stapler 1. As the anvil buttress loading unit 900a is slid away from the surgical stapler 1, the anvil buttress 100a disengages from the body 910a and is retained on the anvil assembly 40 such that the anvil buttress 100a is left loaded on the anvil assembly 40, as seen in FIG. 33.

The cartridge assembly 50 is then loaded in a similar manner. The user grasps the body 910b of the cartridge buttress loading unit 900b and manipulates the body 910b onto the cartridge assembly 50 by aligning the buttress cavity 911b of the cartridge buttress loading unit 900b with the distal end of the cartridge assembly 50 and sliding the cartridge buttress loading unit 900b over the cartridge assembly 50 until the cartridge assembly 50 is received within the buttress cavity 911b and thus, the tubular body 110b of the cartridge buttress 100b. The clip 130 is then detached from the body 910b and pulled proximally towards the user thereby unfurling the strap 102b from the strap cavity 135 of the clip 130. The clip 130 is secured to the elongate tubular body portion 20 of the surgical stapler 1, as described above, with respect to the clip 130 of the anvil buttress 100a, and then the body 910b of the cartridge buttress loading unit 900b is slid distally off of the cartridge assembly 50. As the cartridge buttress loading unit 900b is slid away from the surgical stapler 1, the cartridge buttress 100b disengages the body 910b and is retained on the cartridge assembly 50 such that the surgical buttress 100b is left loaded on the cartridge assembly 50. The surgical stapler 1, loaded with the anvil and cartridge buttresses 100a, 100b, as shown in FIG. 33, is now ready for use.

While the surgical buttress loading units have been shown housing the anvil and cartridge buttresses 100a, 100b, it should be understood that the surgical buttress loading units may be utilized with a variety of surgical buttresses suitable for use with an anvil and/or staple cartridge assembly of a surgical stapler.

It should be further understood that the surgical buttresses applicators described herein may be used with other surgical apparatus, such as electromechanical surgical devices as described, for example, in U.S. Patent Appl. Pub. Nos. 2015/0157320, 2015/0157321, and 2018/0360460, the entire contents of each of which are incorporated herein by reference.

The surgical buttress may be provided and/or sold as part of a surgical buttress loading assembly that includes the surgical buttress and the surgical buttress applicator. Alternatively, the surgical buttress and the surgical buttress applicator may be provided and/or sold separately and assembled by the user. In embodiments, one or more surgical buttresses and one or more surgical buttress applicators are provided in a kit. In some embodiments, the kit further includes one or more end effectors and, in certain embodiments, the kit further includes a surgical stapler.

In any of the embodiments disclosed herein, the surgical buttress can include, or be used with, brachytherapy, chemotherapy, other medical materials or pharmaceuticals. The buttress portion or body of the surgical buttress can have pockets, apertures, or other features for retaining brachytherapy seeds with the buttress portion, or brachytherapy seeds or materials can be incorporated into a suture or sutures that are threaded into or through the buttress portion or otherwise attached thereto. A coating having brachytherapy materials can be applied to a buttress portion or body of a surgical buttress by spraying or dipping. Chemotherapy pharmaceuticals or agents can be incorporated into the buttress portion of the surgical buttress, coated thereon, or applied as part of a suture or suture or other feature.

While several embodiments of the disclosure have been shown in the drawings, it is not intended that the disclosure be limited thereto, as it is intended that the disclosure be as broad in scope as the art will allow and that the specification be read likewise. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Therefore, the above description should not be construed as limiting, but merely as exemplifications of preferred embodiments. Thus the scope of the embodiments should be determined by the appended claims and their legal equivalents, rather than by the examples given.

What is claimed is:

1. A surgical buttress loading assembly comprising:
   a surgical buttress applicator including:
      an anvil buttress loading unit defining a buttress cavity and a strap cavity therein; and
      a cartridge buttress loading unit defining a buttress cavity and a strap cavity therein;
   an anvil buttress including:
      a tubular body disposed within the buttress cavity of the anvil buttress loading unit; and
      a strap extending from the tubular body of the anvil buttress and positioned within the strap cavity of the anvil buttress loading unit; and
   a cartridge buttress including:
      a tubular body disposed within the buttress cavity of the cartridge buttress loading unit; and
      a strap extending from the tubular body of the cartridge buttress and positioned within the strap cavity of the cartridge buttress loading unit.

2. The surgical buttress loading assembly of claim 1, further comprising a first clip secured to the strap of the anvil buttress and a second clip secured to the strap of the cartridge buttress.

3. The surgical buttress loading assembly of claim 2, wherein the first and second clips are releasably secured to the respective anvil and cartridge buttress loading units.

4. The surgical buttress loading assembly of claim 3, wherein the first and second clips are each partially disposed within the strap cavity of the respective anvil and cartridge buttress loading units.

5. The surgical buttress loading assembly of claim 2, wherein the first clip blocks the buttress cavity of the cartridge buttress loading unit.

6. The surgical buttress loading assembly of claim 5, wherein the first clip partially extends into the buttress cavity of the cartridge buttress loading unit.

7. The surgical buttress loading assembly of claim 5, wherein the first clip extends laterally across the buttress cavity of the cartridge buttress loading unit and the second clip extends longitudinally from the buttress cavity of the cartridge buttress loading unit.

8. The surgical buttress loading assembly of claim 1, wherein each of the anvil and cartridge buttress loading units includes first and second tabs extending proximally from the respective buttress cavities, the first and second tabs configured to engage the respective anvil and cartridge buttresses to retain the tubular body portions within the buttress cavity in an open configuration.

9. The surgical buttress loading assembly of claim 1, wherein the anvil buttress loading unit is disposed proximal of the cartridge buttress loading unit.

10. The surgical buttress loading assembly of claim 1, wherein the anvil and cartridge buttress loading units are separate from each other and each includes indicia indicating a loading sequence onto a surgical stapler.

11. The surgical buttress loading assembly of claim 1, wherein a hinge interconnects the anvil and cartridge buttress loading units about a distal end portion of the surgical buttress applicator so that the anvil and cartridge buttress loading units are movable between approximated and unapproximated positions.

12. The surgical buttress loading assembly of claim 1, wherein a hinge interconnects the anvil and cartridge buttress loading units such that in a first position, the anvil buttress loading unit is longitudinally aligned with the cartridge buttress loading unit and blocks the buttress cavity of the cartridge buttress loading unit and, in a second position, the anvil buttress loading unit is rotated laterally so that the buttress cavity of the cartridge buttress loading unit is unblocked.

13. The surgical buttress loading assembly of claim 1, wherein the anvil and cartridge buttress loading units are longitudinally slidable relative to each other such that in a first position, the anvil buttress loading unit is proximal of the cartridge buttress loading unit and, in a second position, the anvil and cartridge buttress loading units are aligned.

\* \* \* \* \*